(12) United States Patent
Ung et al.

(10) Patent No.: US 12,064,362 B2
(45) Date of Patent: Aug. 20, 2024

(54) IMPLANT TISSUE PROTECTION TOOL

(71) Applicant: Medtronic, Inc., Minneapolis, MN (US)

(72) Inventors: Victoria Ung, Novato, CA (US); James E. Mitchell, Windsor, CA (US); Kshitija P. Garde, Fullerton, CA (US); Philip C. Leung, Midway City, CA (US); Justin R. Peterson, Santa Rosa, CA (US); Priyanka Ganesh, Irvine, CA (US); Nirav P. Patel, Irvine, CA (US); Karl L. Olney, Irvine, CA (US); Veronica Woen, Westminster, CA (US)

(73) Assignee: Medtronic, Inc., Minneapolis, MN (US)

( * ) Notice: Subject to any disclaimer, the term of this patent is extended or adjusted under 35 U.S.C. 154(b) by 373 days.

(21) Appl. No.: 17/668,167

(22) Filed: Feb. 9, 2022

(65) Prior Publication Data
US 2022/0273476 A1    Sep. 1, 2022

Related U.S. Application Data

(60) Provisional application No. 63/155,158, filed on Mar. 1, 2021.

(51) Int. Cl.
*A61F 2/95* (2013.01)
*A61F 2/24* (2006.01)
(52) U.S. Cl.
CPC .......... *A61F 2/9524* (2020.05); *A61F 2/2418* (2013.01); *A61F 2/2436* (2013.01)
(58) Field of Classification Search
CPC ..... A61F 2/9524; A61F 2/2418; A61F 2/2436
See application file for complete search history.

(56) References Cited

U.S. PATENT DOCUMENTS

2013/0310926 A1\* 11/2013 Hariton ................... E03C 1/025
                                                       623/2.11
2015/0320556 A1    11/2015 Levi et al.
(Continued)

FOREIGN PATENT DOCUMENTS

WO    WO-2009-149462 A2    12/2009

OTHER PUBLICATIONS

International Search Report & Written Opinion, International Application No. PCT/IB2022/051787 mailed on Jun. 24, 2022, 15 pages.

*Primary Examiner* — Suba Ganesan
(74) *Attorney, Agent, or Firm* — Medler Ferro Woodhouse & Mills PLLC

(57) ABSTRACT

Novel tools and techniques are provided for implementing protection of at least one tissue layer of a medical device or implant during crimping of the medical device or implant. In various embodiments, an implant tissue protection tool may include an outer portion configured to surround one or more outer segments of at least one tissue layer of a medical device to be implanted into a body of a subject and at least one protrusion (which may be affixed to a surface of the outer portion) configured to minimize or prevent occurrence (or likelihood of occurrence) of the at least one tissue layer (in some cases, leaflet material, or the like) of the medical device passing through at least one opening defined by a frame structure of the medical device during crimping of the medical device by a crimping device in preparation for implantation into the body of the subject.

25 Claims, 23 Drawing Sheets

(56) References Cited

U.S. PATENT DOCUMENTS

2018/0133000 A1 5/2018 Scheinblum et al.
2018/0325665 A1 11/2018 Gurovich et al.
2019/0053895 A1 2/2019 Levi

* cited by examiner

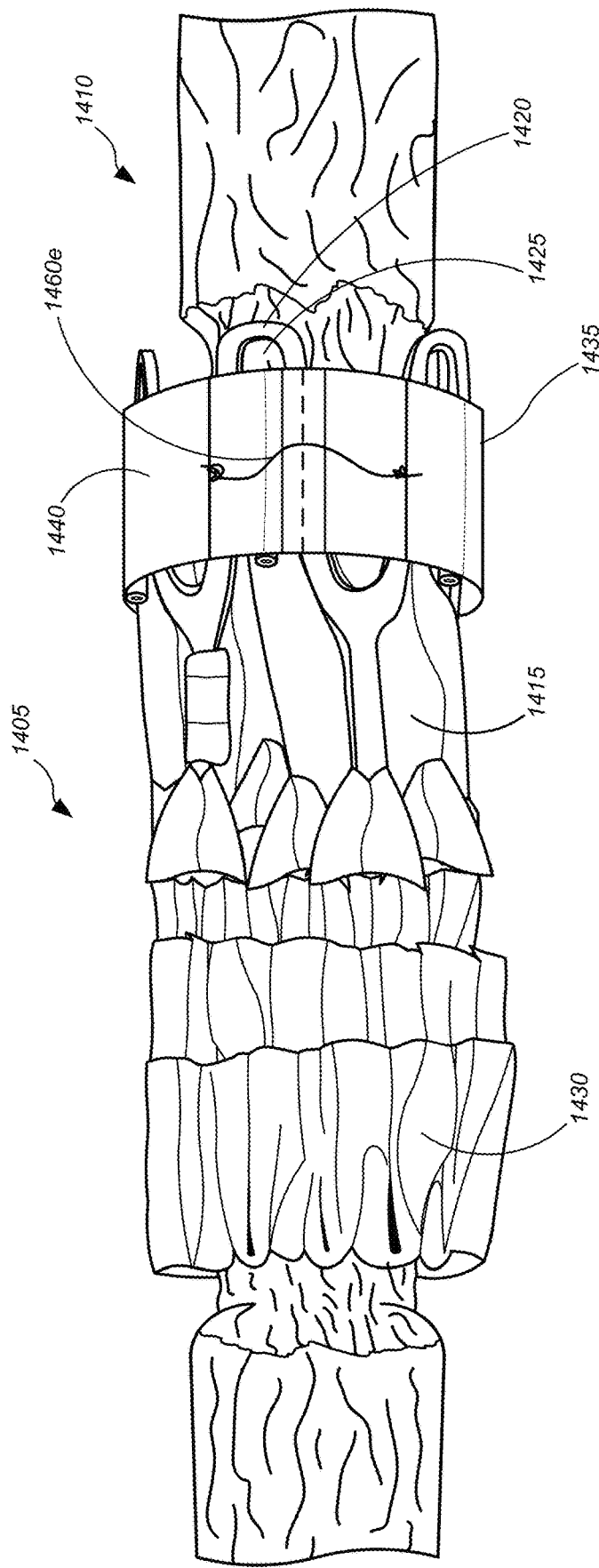

IMPLANT TISSUE PROTECTION TOOL

CROSS-REFERENCES TO RELATED APPLICATIONS

This application claims priority to U.S. Patent Application Ser. No. 63/155,158 (the "'158 Application"), filed Mar. 1, 2021, by Victoria Ung et al., entitled, "Implant Tissue Protection Tool," the disclosure of which is incorporated herein by reference in its entirety for all purposes.

This application may also be related to U.S. Patent Application Ser. No. 62/985,131 (the "'131 Application"), filed Mar. 4, 2020, by Justin Peterson, entitled, "Balloon Expandable Stent with Lengthened Commissure Posts for Transcatheter Implantation of a Cardiac Valve Prosthesis," the disclosure of which is incorporated herein by reference in its entirety for all purposes.

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing crimping of a medical device or implant for placement of the medical device or implant in a subject's body, and, more particularly, to methods, systems, and apparatuses for implementing protection of at least one tissue layer of a medical device or implant during crimping of the medical device or implant.

BACKGROUND

Medical devices—including, but not limited to, stents, prosthetic valves, and other implantable medical devices, can be compressed to facilitate delivery of such medical devices at one or more implantation sites in the body of a subject (e.g., a native cardiac valve, or the like). Each medical device is delivered to an implantation site using a delivery device (such as a catheter, for example) that has radial dimensions that are smaller than the unconstrained or expanded radial dimensions of the medial device and/or that are smaller than the dimensions of the medical device upon deployment of the medical device at the implantation site. To facilitate insertion of such a medical device into or on the delivery device, the medical device is compressed (typically, at least radially). Such radial compression is known as crimping.

However, typical features of medical devices for implantation in the body of subjects make some designs more susceptible to pinching of components (e.g., leaflets of valvular implants, or the like). Such typical features might include, without limitation, large outflow frame cells or openings, wide leaflets, long leaflets, and/or the like. In some cases, procedural effects—including, but not limited to, high crimp forces, or the like—may contribute to risk of pinching of components of the medical devices, such as leaflet pinching, in which leaflets become caught between two or more struts as the medical device or implant is crimped to its final profile. The immediate effect seen is leaflet peeling and cuts. The damage produced from such action can result in long term durability issues for the medical device and its functionality.

Hence, there is a need for more robust and scalable solutions for implementing crimping of a medical device or implant for placement of the medical device or implant in a subject's body, and, more particularly, to methods, systems, and apparatuses for implementing protection of at least one tissue layer of a medical device or implant during crimping of the medical device or implant.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 14A-14I are diagrams illustrating various non-limiting examples of an implant tissue protection tool, including at least one separation device, that may be used to protect at least one tissue layer of a medical device during crimping of the medical device prior to implantation of the medical device within a body of a subject, in accordance with various embodiments.

DETAILED DESCRIPTION OF CERTAIN EMBODIMENTS

Overview

Figure 1A:
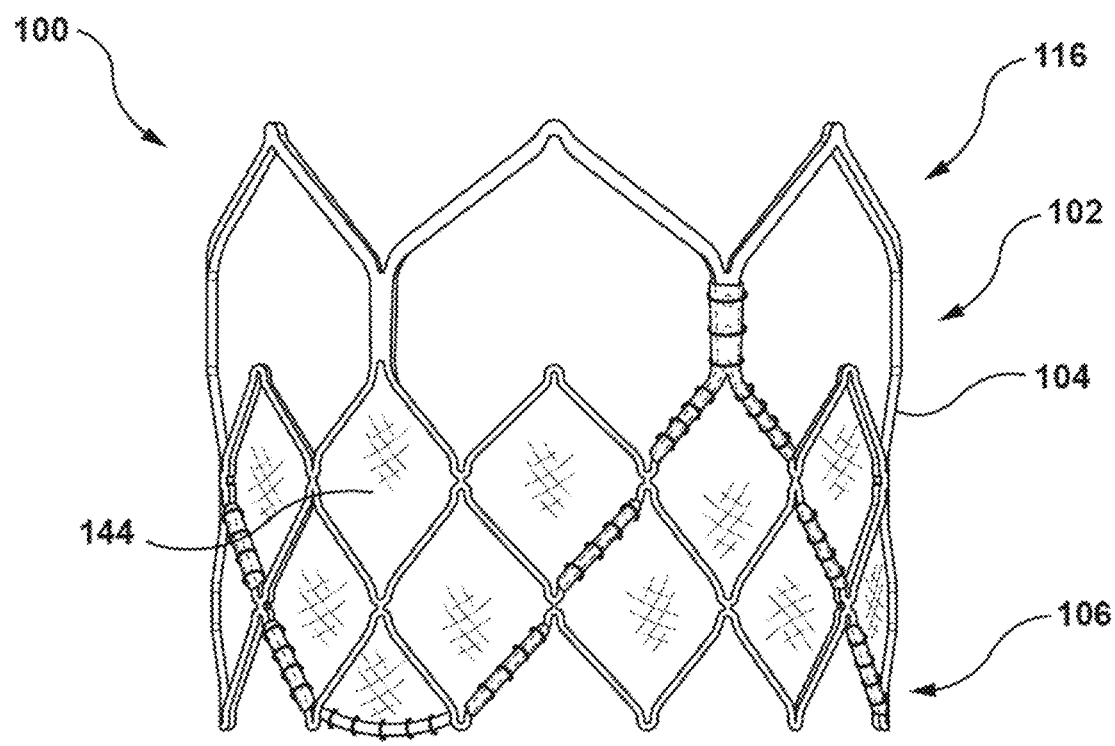
FIG. 1A is a schematic diagram illustrating a side view of a non-limiting example of a transcatheter valve prosthesis in an expanded configuration, in accordance with various embodiments.

Various embodiments provide tools and techniques for implementing crimping of a medical device or implant for placement of the medical device or implant in a subject's body, and, more particularly, to methods, systems, and apparatuses for implementing protection of at least one tissue layer of a medical device or implant during crimping of the medical device or implant.

In various embodiments, an assembly may comprise a medical device (in some cases, a transcatheter valve prosthesis, or the like, although not limited to such) and an implant tissue protection tool (in this case, a leaflet protection tool, or the like, although not limited to such). The medical device may include, without limitation, at least one tissue layer (in this case, a prosthetic valve, or the like, which may include one or more leaflets or leaflet structures, or the like) and a stent or frame (which may include a plurality of struts, a plurality of crowns, and/or a plurality of axial frame members, and/or the like). The stent or frame may include a plurality of openings or cells that are defined at least in part by two or more struts among the plurality of struts (and, in some cases, also by one or more crowns among the plurality of crowns and/or by one or more axial frame members among the plurality of axial frame members, and/or the like). In some instances, the stent or frame may further include an inflow portion and an outflow portion, with the inflow portion being substantially covered by at least an outer skirt (and, in some cases, also by an inner skirt). Outflow openings, which are not covered by a skirt (whether outer or inner skirt), may present a pinch risk during crimping of the medical device for delivery to an implantation site (e.g., a native heart valve, or other suitable implantation site, or the like) in a body of a subject, due to its design, particularly if the outflow openings defined at least in part by the two or more struts (and, in some cases, the one or more crowns and/or the one or more axial frame members, and/or the like) in the outflow portion of the stent or frame is substantially larger than the inflow openings defined by corresponding struts (and, in some cases, crowns) in the inflow portion of the stent or frame.

The implant tissue protection tool—which may include, but is not limited to, an outer portion and at least one protrusion affixed to a first surface of the outer portion (in some cases, integrally formed from the outer portion, or the like). The outer portion may be configured to surround one or more outer segments of the at least one tissue layer of the medical device to be implanted into the body of the subject. The at least one protrusion may be configured to minimize (and, in some cases, prevent) occurrence (or likelihood of occurrence) of the at least one tissue layer (in some cases, leaflet material, or the like) of the medical device passing through at least one opening defined by a frame structure of the medical device during crimping of the medical device by a crimping device in preparation for implantation into the body of the subject. That is, the at least one protrusion may be configured to actively push radially inward against the at least one tissue layer of the medical device to minimize (and, in some cases, prevent) pinching of the at least one tissue layer (e.g., leaflet material, or the like) by two or more struts (or other stent or frame structure) of the medical device while the medical device is being crimped in preparation for delivery of the medical device to an implantation site within the body of the subject. The implant tissue protection tool described herein is separate from, and has a structure as a whole that is independent of, the crimping device.

These and other aspects of the implant tissue protection tool and/or the method for implementing the implant tissue protection tool are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) computer-performed methods, and/or computer systems, represent tangible, concrete improvements to existing technological areas, including, without limitation, medical implant technology, and/or the like. In other aspects, certain embodiments, can improve the functioning of user equipment or systems themselves (e.g., medical implant systems and components, etc.), for example, by utilizing an implant tissue protection tool that comprises an outer portion that is configured to surround one or more outer segments of at least one tissue layer of a medical device to be implanted into a body of a subject; and at least one protrusion affixed to a first surface of the outer portion, the at least one protrusion being configured to prevent the at least one tissue layer of the medical device from passing through at least one opening defined at least in part by two or more struts of the medical device during crimping of the medical device by a crimping device in preparation for implantation into the body of the subject, wherein the implant tissue protection tool is separate from, and has a structure as a whole that is independent of, the crimping device, and/or the like.

In particular, to the extent any abstract concepts are present in the various embodiments, those concepts can be implemented as described herein by devices, systems, and methods that involve specific novel functionality (e.g., steps or operations), such as, using the structure of the implant tissue protection tool (as described above) to prevent the at least one tissue layer of the medical device from passing through at least one opening defined at least in part by two or more struts of the medical device during crimping of the medical device by the crimping device in preparation for implantation into the body of the subject, and/or the like. These functionalities can produce tangible results outside of the implementing computer system, including, merely by way of example, prevention of damage to the at least one tissue layer of the medical device during crimping, and/or the like, resulting in prolonged life and functionality of the medical device (or implant), at least some of which may be observed or measured by subjects and/or healthcare providers.

In an aspect, an implant tissue protection tool may comprise an outer portion that is configured to surround one or more outer segments of at least one tissue layer of a medical device to be implanted into a body of a subject, wherein the medical device comprises a frame with a plurality of struts; and at least one protrusion affixed to a first surface of the outer portion, the at least one protrusion being configured to minimize occurrence of the at least one tissue layer of the medical device passing through at least one opening defined at least in part by two or more struts of the medical device during crimping of the medical device by a crimping device in preparation for implantation into the body of the subject.

According to some embodiments, the implant tissue protection tool may be separate from, and may have a structure as a whole that is independent of, the crimping device. In some embodiments, the outer portion comprises a sleeve that may be configured to fit snugly over an outer perimeter of the medical device, wherein the at least one protrusion may be configured to extend radially inward through the at least one opening that is not covered by a skirt layer of the medical device. In some instances, wherein the sleeve may have a longitudinal length that covers at least a portion of a longitudinal length of the medical device, the longitudinal length of the sleeve being configured to at least partially cover all openings defined at least in part by struts of the medical device that are not covered by the skirt layer.

According to some embodiments, the at least one protrusion may comprise a plurality of protrusions affixed to the inner surface of the sleeve, wherein at least one protrusion among the plurality of protrusions may be configured to extend through each opening defined at least in part by struts of the medical device that are not covered by the skirt layer. In some cases, the at least one protrusion among the plurality of protrusions that may be configured to extend through each opening defined at least in part by the struts of the medical device that are not covered by the skirt layer may comprise two protrusions that are configured to extend through each opening. Alternatively, or additionally, each of the plurality of protrusions may have a length that is similar to a longitudinal length of the sleeve, wherein the length of each protrusion may be aligned with the longitudinal length of the sleeve when each of the plurality of protrusions is affixed to the sleeve, and wherein the length of each of the at least one protrusion may be configured to fit within each of the openings defined at least in part by struts of the medical device that are not covered by the skirt layer.

In some embodiments, the implant tissue protection tool may be selectable from among a plurality of versions of the implant tissue protection tool, each version having a different combination of depth and thickness of each of the at least one protrusion, wherein the implant tissue protection tool may be selectable with appropriate depth and thickness of each of the at least one protrusion to minimize occurrence of the at least one tissue layer of the medical device passing through the at least one opening during crimping of the medical device, wherein the depth of each protrusion may extend radially inward and the thickness may extend in a direction parallel to a tangent from the outer portion.

Merely by way of example, in some cases, each of the at least one protrusion may have a hollow cylindrical shape. Alternatively, each of the at least one protrusion may have a flared hollow polygonal prism shape.

According to some embodiments, the implant tissue protection tool may further comprise a plurality of clips, wherein each clip may comprise a connecting portion forming part of the outer portion, wherein the at least one protrusion may comprise at least two protrusions extending from each connecting portion of each clip. In some cases, the plurality of clips may be connected together along the connecting portions.

In some embodiments, the at least one protrusion may comprise a plurality of protrusions, wherein the outer portion and the plurality of protrusions may be integrally formed using a pliable material. In some instances, the implant tissue protection tool may be configured to wrap around the outer perimeter of the medical device, with the plurality of protrusions each being configured to extend through the at least one opening that is not covered by a skirt layer. Alternatively, or additionally, the implant tissue protection tool may be configured to be wedged between the one or more outer segments of the at least one tissue layer and the two or more struts of the medical device, with the plurality of protrusions each being configured to extend along a direction that is either parallel with or at a small angle with respect to an axis of the medical device, wherein the integrally formed outer portion and plurality of protrusions are configured to be disposed between the one or more outer segments of the at least one tissue layer and the two or more struts of the medical device, without the plurality of protrusions extending longitudinally beyond a longitudinal length of the medical device when fully wedged between the one or more outer segments of the at least one tissue layer and the two or more struts of the medical device.

According to some embodiments, the at least one protrusion may comprise a plurality of protrusions, wherein the outer portion and the plurality of protrusions may be integrally formed as a flat continuous band, wherein the plurality of protrusions may be each formed by folding the flat continuous band in on itself, with the outer portion being configured to wrap around an outer perimeter of the medical device and with at least one protrusion among the plurality of protrusions being configured to extend through each of the at least one opening that is not covered by a skirt layer.

In some embodiments, the implant tissue protection tool may be made of a material that is the same as a material from which the at least one tissue layer is made. Alternatively, or additionally, the implant tissue protection tool may be made of a material comprising at least one of animal tissue, bovine pericardium, porcine pericardium, open-cell foam, polyurethane foam, fabric, or expanded polytetrafluoroethylene ("ePTFE"), and/or the like.

According to some embodiments, crimping of the medical device may comprise a partial crimp that reduces a first diameter of the medical device to a second diameter smaller than the first diameter and a final crimp that reduces the second diameter of the medical device to a third diameter smaller than the second diameter, wherein the implant tissue protection tool may be separated from the medical device after the partial crimp and before the final crimp.

In some embodiments, the implant tissue protection tool may further comprise at least one separation device affixed to the outer portion, the at least one separation device being configured to facilitate efficient separation of the implant tissue protection tool from the medical device and to facilitate preferential orientation or folding direction of the at least one tissue layer of the medical device and/or components of the medical device. In some cases, the at least one separation device may comprise a plurality of separation devices that is affixed to and arranged at intervals around an outer perimeter of the outer portion. In some instances, the at least one separation device has a form type or shape comprising one of a side loop configuration, a bunny ear configuration, an upper tab configuration, a basket handle configuration, or a suture loop configuration, and/or the like. Alternatively, or additionally, the at least one separation device has a general form type or shape comprising one of a loop configuration or a tab configuration, or the like. The loop configuration (which may include, without limitation, the side loop configuration, a basket handle configuration, or a suture loop configuration, etc.) may comprise a center area without any material and may be bound at the edges. The tab configuration (which may include, but is not limited to, the bunny ear configuration, the upper tab configuration, etc.) may be without a center opening. In some cases, the shape of the at least one separation device may comprise any suitable shape including, without limitation, polygonal, circular, elliptical, and/or the like. According to some embodiments, the implant tissue protection tool may be made of a material that is capable of being perforated and torn, wherein the outer portion may include a perforation along an entire longitudinal length thereof.

In another aspect, a medical device for implantation into a body of a subject, the medical device may comprise: at least one tissue layer; a plurality of struts; and an implant tissue protection tool. The implant tissue protection tool may comprise: an outer portion that may be configured to surround one or more outer segments of the at least one tissue layer of the medical device; and at least one protrusion affixed to a first surface of the outer portion, the at least one protrusion being configured to minimize occurrence of the at least one tissue layer of the medical device passing through at least one opening defined at least in part by two or more struts among the plurality of struts of the medical device during crimping of the medical device by a crimping device in preparation for implantation into the body of the subject, wherein the implant tissue protection tool is separate from, and has a structure as a whole that is independent of, the crimping device, wherein the implant tissue protection tool may be configured to be separated from the remainder of the medical device prior to implantation of the medical device into the body of the subject.

In yet another aspect, a method may comprise: forming an assembly by inserting a delivery system axially through a middle portion of a medical device to be implanted into a body of a subject, the medical device having an implant tissue protection tool removably affixed thereto, wherein the implant tissue protection tool comprises an outer portion that is configured to surround one or more outer segments of at least one tissue layer of the medical device and at least one protrusion affixed to a first surface of the outer portion. The method may further comprise inserting the assembly into a crimping device, wherein the implant tissue protection tool is separate from, and has a structure as a whole that is independent of, the crimping device; performing a partial crimp of the assembly, using the crimping device, to reduce a first diameter of the assembly to a second diameter smaller than the first diameter, wherein, during the partial crimp, the at least one protrusion actively pushes radially inward on the at least one tissue layer, thereby minimizing occurrence of the at least one tissue layer of the medical device passing through at least one opening defined at least in part by two or more struts of the medical device during crimping of the medical device; and removing the implant tissue protection tool. The method may further comprise adjusting a position of the medical device on the delivery system; and performing a final crimp of the assembly, without the implant tissue protection tool and using the crimping device, to reduce the second diameter of the assembly to a third diameter smaller than the second diameter, in preparation for implantation of the medical device into the body of the subject.

In some embodiments, the crimping device may comprise one of an automated crimping device, a mechanical-assist crimping device, a manual crimping device, or a tapered capsule-based passive crimping device, and/or the like. According to some embodiments, the method may further comprise removably affixing the implant tissue protection tool to the medical device prior to forming the assembly. In some instances, the at least one protrusion may be further configured to prevent the at least one tissue layer of the medical device from passing through at least one opening defined at least in part by two or more struts of the medical device during crimping of the medical device by the crimping device in preparation for implantation into the body of the subject.

In yet another aspect, a transcatheter valve prosthesis system may comprise a transcatheter valve prosthesis and a leaflet protection tool. The transcatheter valve prosthesis may comprise a stent having a crimped configuration for delivery within a vasculature and an expanded configuration for deployment within a native heart valve of a subject, and a prosthetic valve disposed within and secured to at least a transition portion of the stent. The stent may comprise an inflow portion including at least three rows of struts and crowns formed between adjacent pairs of said struts, the inflow portion further including a plurality of inflow openings each defined at least in part by arrangement of the struts and crowns, wherein the at least three rows of the inflow portion are formed between an inflow end of the axial frame members and an inflow end of the stent; an outflow portion including a single row of struts and crowns formed between adjacent pair of said struts, the outflow portion further including a plurality of outflow openings each defined at least in part by arrangement of the struts and crowns of the inflow portion and the struts and crowns of an adjacent row of the inflow portion, the outflow portion being coupled to an outflow end of the axial frame members, wherein exactly two struts of the plurality of struts of the outflow portion are disposed between adjacent axial frame members; and a plurality of axial frame members, wherein at least two of the plurality of the axial frame members are commissure posts having a first end connected to a crown of the inflow portion and an unattached second end disposed within the outflow portion such that a pair of struts of the outflow portion intersect each commissure post at a mid-portion thereof, wherein a directional marker is formed on at least one commissure post. The prosthetic valve may comprise two or more leaflets and may be configured to substantially block blood flow in one direction using the two or more leaflets to regulate blood flow through a central lumen of the stent.

The leaflet protection tool may comprise an outer portion that is configured to surround one or more outer segments of the prosthetic valve of the transcatheter valve prosthesis to be deployed within the native heart valve; and at least one protrusion affixed to a first surface of the outer portion, the at least one protrusion being configured to minimize occurrence of any of the two or more leaflets passing through at least one outflow opening during crimping of the transcatheter valve prosthesis by a crimping device in preparation for implantation into a body of the subject, by actively pushing the two or more leaflets radially inward during crimping, wherein the leaflet protection tool may be separate from, and may have a structure as a whole that is independent of, the crimping device, wherein the leaflet protection tool may be configured to be separated from the transcatheter valve prosthesis prior to implantation of the transcatheter valve prosthesis into the body of the subject.

In another aspect, a transcatheter valve prosthesis system may comprise a transcatheter valve prosthesis and a leaflet protection tool. The transcatheter valve prosthesis may comprise a stent having a crimped configuration for delivery within a vasculature and an expanded configuration for deployment within a native heart valve of a subject, and a prosthetic valve disposed within and secured to at least a transition portion of the stent. The stent may comprise an inflow portion formed proximate to an inflow end of the stent, the inflow portion including a plurality of crowns and a plurality of struts with each crown being formed between a pair of opposing struts, a plurality of inflow side openings being defined at least in part by the plurality of crowns and the plurality of struts of the inflow portion, wherein endmost inflow side openings and endmost inflow crowns are formed at the inflow end of the stent; an outflow portion formed proximate to an outflow end of the stent, the outflow portion including a plurality of crowns and a plurality of struts with each crown being formed between a pair of opposing struts, a plurality of outflow side openings being defined at least in part by the plurality of crowns and the plurality of struts of the outflow portion, wherein endmost outflow crowns may be formed at the outflow end of the stent; and the transition portion extending between the inflow portion and the outflow portion, the transition portion including a plurality of axial frame members, wherein at least two of the plurality of the axial frame members may be commissure posts having a first end connected to a crown of the inflow portion and an unattached second end disposed within the outflow portion such that a pair of struts of the outflow portion intersect each commissure post at a mid-portion thereof. The prosthetic valve may comprise two or more leaflets and may be configured to substantially block blood flow in one direction using the two or more leaflets to regulate blood flow through a central lumen of the stent.

The leaflet protection tool may comprise an outer portion that is configured to surround one or more outer segments of the prosthetic valve of the transcatheter valve prosthesis to be deployed within the native heart valve; and at least one protrusion affixed to a first surface of the outer portion, the at least one protrusion being configured to minimize occurrence of any of the two or more leaflets passing through at least one outflow side opening during crimping of the transcatheter valve prosthesis by a crimping device in preparation for implantation into a body of the subject, by actively pushing the two or more leaflets radially inward during crimping, wherein the leaflet protection tool may be separate from, and may have a structure as a whole that is independent of, the crimping device, wherein the leaflet protection tool may be configured to be separated from the transcatheter valve prosthesis prior to implantation of the transcatheter valve prosthesis into the body of the subject.

In some embodiments, an area of each outflow side opening may be greater than an area of each inflow side opening by a ratio of at least 1.5:1. In some instances, the outflow portion may further include 6 outflow side openings, while the inflow portion may further include 12 inflow side openings per row. In some cases, the leaflet protection tool may be made of a material that is the same as a material from which the prosthetic valve is made. Alternatively, or additionally, the leaflet protection tool may be made of a material comprising at least one of animal tissue, bovine pericardium, porcine pericardium, open-cell foam, polyurethane foam, fabric, or expanded polytetrafluoroethylene ("ePTFE"), and/or the like.

According to some embodiments, crimping of the transcatheter valve prosthesis may comprise a partial crimp that reduces a first diameter of the transcatheter valve prosthesis to a second diameter smaller than the first diameter and a final crimp that reduces the second diameter of the transcatheter valve prosthesis to a third diameter smaller than the second diameter, wherein the leaflet protection tool may be separated from the transcatheter valve prosthesis after the partial crimp and before the final crimp.

In yet another aspect, a crimping system may be provided for atraumatic crimping of an implantable prosthetic valve. The crimping system may comprise an implantable prosthetic valve, a crimping apparatus, and a leaflet protection tool. The implantable prosthetic valve may comprise a radially collapsible and expandable annular frame and a leaflet structure mounted inside the frame, the frame comprising a plurality of interconnected struts defining a plurality of open cells in the frame. The crimping apparatus may have a plurality of crimping jaws arranged to form an aperture sized to receive the implantable prosthetic valve in a first, expanded state, to move radially inwardly to radially collapse the implantable prosthetic valve from the first, expanded state to a second, radially collapsed state during a partial crimp, and to move radially inwardly to radially collapse the implantable prosthetic valve from the second, radially collapsed state to a third, radially collapsed state during a final crimp.

The leaflet protection tool may be configured to be positioned between the plurality of crimping jaws of the crimping apparatus and the outside of the frame of the implantable prosthetic valve. The leaflet protection tool may comprise an outer portion that is configured to surround one or more outer segments of the implantable prosthetic valve; and at least one protrusion affixed to a first surface of the outer portion, the at least one protrusion being configured to minimize occurrence of the leaflet structure passing through any of the plurality of open cells in the frame during crimping of the implantable prosthetic valve by the crimping apparatus in preparation for implantation into a body of a subject, by actively pushing the leaflet structure radially inward away from the inside of the frame of the implantable prosthetic valve during the partial crimp, wherein the leaflet protection tool may be separated from the implantable prosthetic valve after the partial crimp and before the final crimp.

In some embodiments, the leaflet protection tool may be made of a material that is the same as a material from which the prosthetic valve is made. Alternatively, or additionally, the leaflet protection tool may be made of a material comprising at least one of animal tissue, bovine pericardium, porcine pericardium, open-cell foam, polyurethane foam, fabric, or expanded polytetrafluoroethylene ("ePTFE"), and/or the like.

According to some embodiments, the implantable prosthetic valve may further comprise an inflow portion including a plurality of inflow open cells among the plurality of open cells in the frame and an outflow portion including a plurality of outflow open cells among the plurality of open cells in the frame, wherein an area of each outflow open cell may be greater than an area of each inflow open cell by a ratio of at least 1.5:1. In some instances, the outflow portion may further include 6 outflow open cells per row, while the inflow portion may further include 12 inflow open cells per row.

In still another aspect, an implantable prosthetic valve system may comprise an implantable prosthetic valve and a leaflet protection tool. The implantable prosthetic valve may comprise a radially collapsible and expandable annular frame and a leaflet structure mounted inside the frame, the frame comprising a plurality of interconnected struts defining a plurality of open cells in the frame. The leaflet protection tool may be configured to be positioned between a plurality of crimping jaws of a crimping apparatus and the outside of the frame of the implantable prosthetic valve, the crimping apparatus having the plurality of crimping jaws arranged to form an aperture sized to receive the implantable prosthetic valve in a first, expanded state, to move radially inwardly to radially collapse the implantable prosthetic valve from the first, expanded state to a second, radially collapsed state during a partial crimp, and to move radially inwardly to radially collapse the implantable prosthetic valve from the second, radially collapsed state to a third, radially collapsed state during a final crimp. The leaflet protection tool may comprise an outer portion that is configured to surround one or more outer segments of the implantable prosthetic valve; and at least one protrusion affixed to a first surface of the outer portion, the at least one protrusion being configured to minimize occurrence of the leaflet structure passing through any of the plurality of open cells in the frame during crimping of the implantable prosthetic valve by the crimping apparatus in preparation for implantation into a body of a subject, by actively pushing the leaflet structure radially inward away from the inside of the frame of the implantable prosthetic valve during the partial crimp, wherein the leaflet protection tool is separated from the implantable prosthetic valve after the partial crimp and before the final crimp.

In some embodiments, the leaflet protection tool may be made of a material that is the same as a material from which the prosthetic valve is made. Alternatively, or additionally, the leaflet protection tool may be made of a material comprising at least one of animal tissue, bovine pericardium, porcine pericardium, open-cell foam, polyurethane foam, fabric, or expanded polytetrafluoroethylene ("ePTFE"), and/or the like.

According to some embodiments, the implantable prosthetic valve may further comprise an inflow portion including a plurality of inflow open cells among the plurality of open cells in the frame and an outflow portion including a plurality of outflow open cells among the plurality of open cells in the frame, wherein an area of each outflow open cell may be greater than an area of each inflow open cell by a ratio of at least 1.5:1. In some instances, the outflow portion may further include 6 outflow open cells per row, while the inflow portion may further include 12 inflow open cells per row.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-16 illustrate some of the features of the method, system, and apparatus for implementing crimping of a medical device or implant for placement of the medical device or implant in a subject's body, and, more particularly, to methods, systems, and apparatuses for implementing protection of at least one tissue layer of a medical device or implant during crimping of the medical device or implant, as referred to above. The methods, systems, and apparatuses illustrated by FIGS. 1-16 refer to examples of different embodiments that include various components and steps, which can be considered alternatives or which can be used in conjunction with one another in the various embodiments. The description of the illustrated methods, systems, and apparatuses shown in FIGS. 1-16 is provided for purposes of illustration and should not be considered to limit the scope of the different embodiments.

Figure 1B:
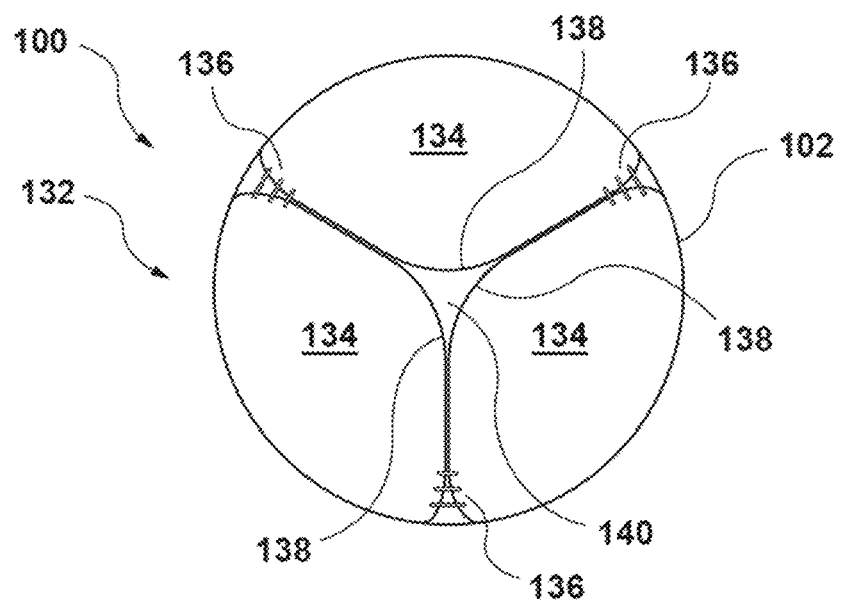
FIG. 1B is a schematic diagram illustrating an end view illustration of the transcatheter valve prosthesis of FIG. 1A.
Figure 1C:
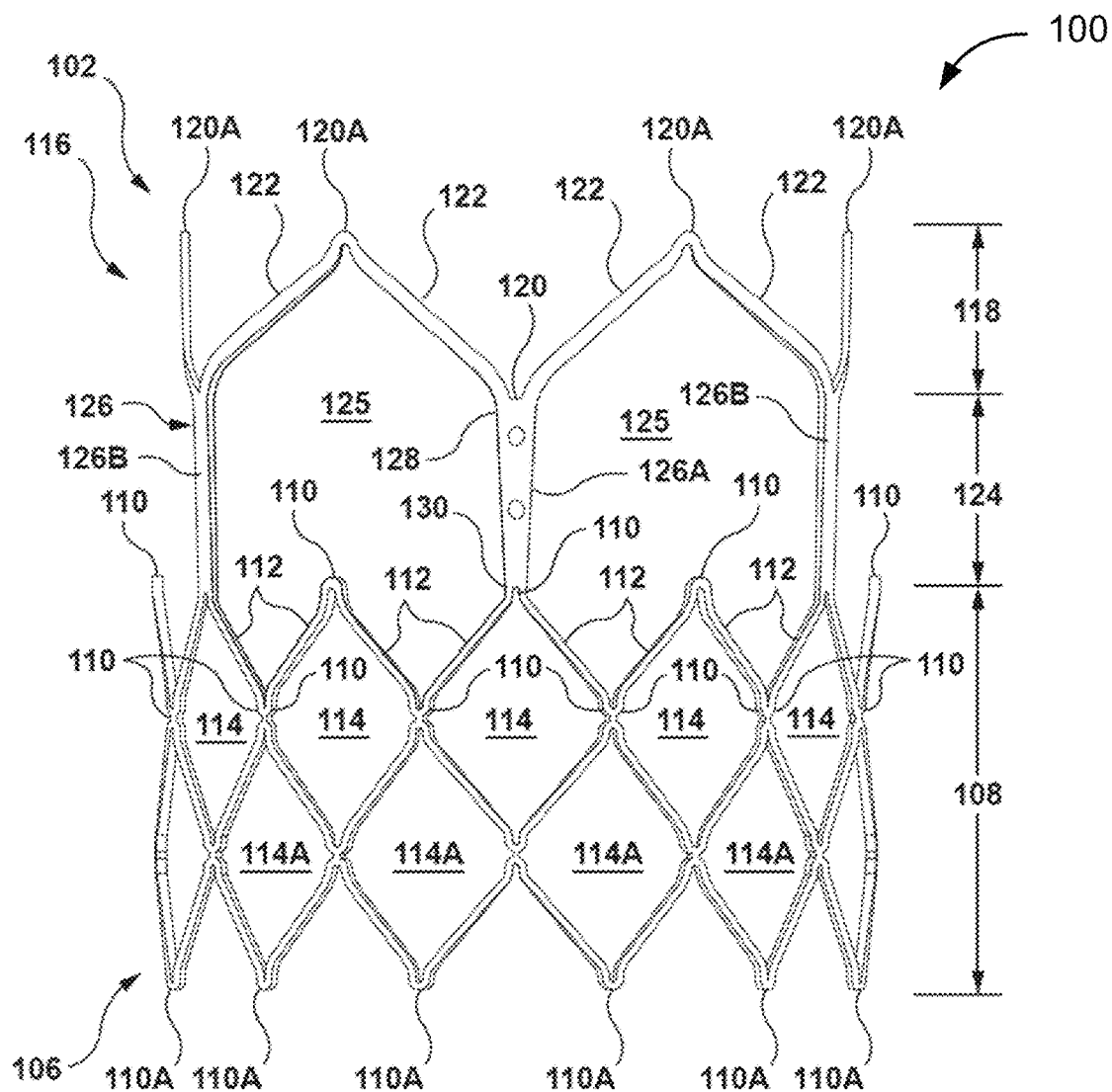
FIG. 1C is a schematic diagram illustrating a side view of the stent or frame of the transcatheter valve prosthesis of FIG. 1A, in the expanded configuration, in accordance with various embodiments.
Figure 1D:
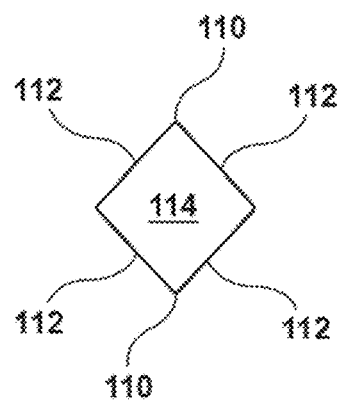
FIG. 1D is a schematic diagram illustrating an enlarged side view of a single cell or side opening of an inflow portion of the stent or frame of the transcatheter valve prosthesis of FIG. 1A, in the expanded configuration, in accordance with various embodiments.
Figure 1E:
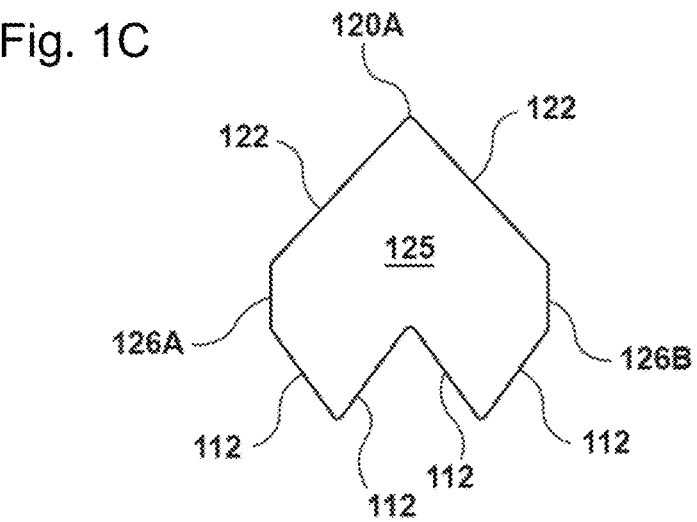
FIG. 1E is a schematic diagram illustrating an enlarged side view of a single endmost or outflow opening of the stent or frame of the transcatheter valve prosthesis of FIG. 1A, in the expanded configuration, in accordance with various embodiments.
Figure 2:
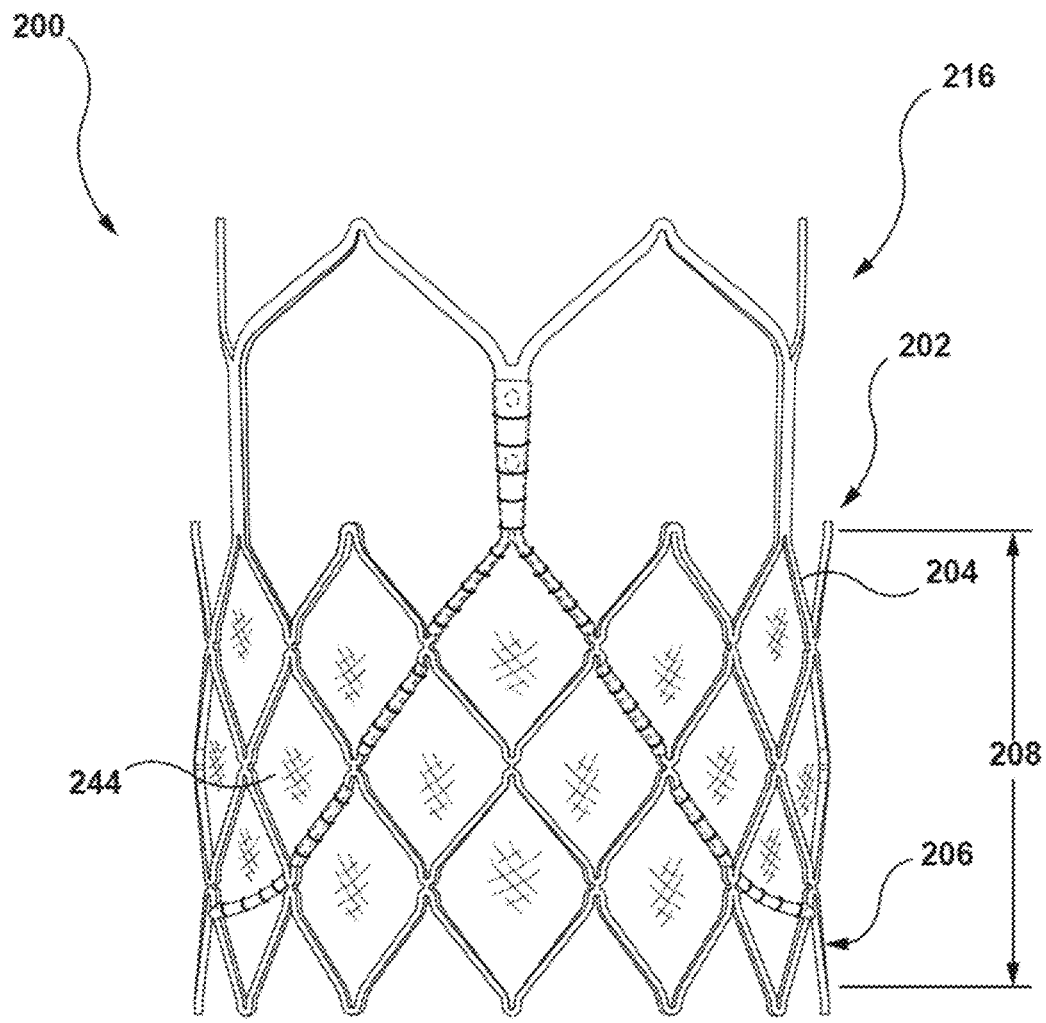
FIG. 2 is a schematic diagram illustrating a side view of another non-limiting example of a transcatheter valve prosthesis in an expanded configuration, in accordance with various embodiments, the transcatheter valve prosthesis of FIG. 2 being relatively longer than the transcatheter valve prosthesis of FIG. 1A.

With reference to the figures, FIGS. 1A-1E (collectively, "FIG. 1") and FIG. 2 depict various non-limiting embodiments 100 and 200 of a transcatheter valve prosthesis with which an implant tissue protection tool described herein may be used, in accordance with various embodiments. The transcatheter valve prosthesis is described in greater detail in the '131 Application, which has already been incorporated by reference in its entirety for all purposes. Although specific structures and configurations are described with reference to the transcatheter valve prosthesis, the various embodiments are not so limited, and the implant tissue protection tool described herein may be used with any suitable design of transcatheter valve prosthesis having any suitable structure or configuration, and in fact may be used with any suitable implantable medical device not limited to transcatheter valve prostheses or the like.

FIG. 1A is a schematic diagram illustrating a side view of a non-limiting example of a transcatheter valve prosthesis in an expanded configuration, in accordance with various embodiments. FIG. 1B is a schematic diagram illustrating an end view illustration of the transcatheter valve prosthesis of FIG. 1A. FIG. 1C is a schematic diagram illustrating a side view of the stent or frame of the transcatheter valve prosthesis of FIG. 1A, in the expanded configuration, in accordance with various embodiments. FIG. 1D is a schematic diagram illustrating an enlarged side view of a single cell or side opening of an inflow portion of the stent or frame of the transcatheter valve prosthesis of FIG. 1A, in the expanded configuration, in accordance with various embodiments. FIG. 1E is a schematic diagram illustrating an enlarged side view of a single endmost or outflow opening of the stent or frame of the transcatheter valve prosthesis of FIG. 1A, in the expanded configuration, in accordance with various embodiments.

With reference to FIG. 1, a transcatheter valve prosthesis 100 might have a radially expandable stent or frame 102 (hereinafter referred to simply as "stent 102") and a prosthetic valve 132. The stent 102 is generally tubular, and is mechanically or balloon expandable, having a crimped configuration for delivery within a vasculature and an expanded configuration for deployment within a native heart valve. FIG. 1A is a side view of the transcatheter valve prosthesis 100 in the expanded configuration, while FIG. 1B is an end view illustration of the transcatheter valve prosthesis 100. When the transcatheter valve prosthesis 100 is deployed within the valve annulus of a native heart valve, the stent 102 of the transcatheter valve prosthesis 100 is configured to be radially expanded within native valve leaflets of the patient's defective valve, to thereby retain the native valve leaflets in a permanently open state. In some embodiments, the transcatheter valve prosthesis 100 is configured for replacement for an aortic valve such that an inflow end 106 of the transcatheter valve prosthesis 100 extends into and anchors within the aortic annulus of a patient's left ventricle, while an outflow end 116 of the transcatheter valve prosthesis 100 is positioned within the aortic sinuses.

The stent 102 of the transcatheter valve prosthesis 100 may be a unitary frame or scaffold that supports the prosthetic valve 132 including one or more valve leaflets 134 within the interior of the stent 102. The prosthetic valve 132 is capable of blocking flow in one direction to regulate flow there-through via the valve leaflets 134 that may form a bicuspid or tricuspid replacement valve. FIG. 1B is an end view of FIG. 1A taken from the outflow end 116 of the prosthesis and illustrates an exemplary tricuspid valve having three valve leaflets 134, although a bicuspid leaflet configuration may alternatively be used in some embodiments. More particularly, as the transcatheter valve prosthesis 100 is configured for placement within a native aortic valve which typically has three leaflets, the prosthetic valve 132 may include three valve leaflets 134. However, the transcatheter valve prosthesis 100 is not required to have the same number of leaflets as the native valve. If the transcatheter valve prosthesis 100 is alternatively configured for placement within a native valve having two leaflets such as the mitral valve, the prosthetic valve 132 may include two or three valve leaflets. The valve leaflets 134 may be attached to a graft material 144 which encloses or lines a portion of the stent 102 as would be known to one of ordinary skill in the art of prosthetic tissue valve construction. The valve leaflets 134 are sutured or otherwise securely and sealingly attached along their bases to the interior surface of the graft material 144, or otherwise attached to the stent 102. Adjoining pairs of leaflets are attached to one another at their lateral ends to form commissures 136, with free edges 138 of the valve leaflets 134 forming coaptation edges that meet in area of coaptation 140.

Graft material 144 may enclose or line the stent 102 as would be known to one of ordinary skill in the art of prosthetic tissue valve construction. Graft material 144 may be a natural or biological material such as pericardium or another membranous tissue such as intestinal submucosa. Alternatively, graft material 144 may be a low-porosity woven fabric, such as polyester, Dacron fabric, or PTFE, which creates a one-way fluid passage when attached to the stent 102. In one embodiment, graft material 144 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Delivery of the transcatheter valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, the transcatheter valve prosthesis 100 remains compressed until it reaches a target diseased native heart valve, at which time a balloon of a delivery system is inflated in order to radially expand the transcatheter valve prosthesis 100 in situ. The delivery system is then removed and the transcatheter valve prosthesis 100 remains deployed within the native target heart valve.

The stent 102 will now be described in more detail. The stent 102 includes an inflow portion 108, an outflow portion 118, and a transition portion 124 bridging, connecting, or otherwise extending between the inflow portion 108 and the outflow portion 118. The stent 102 is a tubular component defining a central lumen or passageway, and further defines the inflow or proximal end 106 and the outflow or distal end 116 of the transcatheter valve prosthesis 100. When expanded, a diameter DI of the inflow end 106 of the stent 102 is substantially the same as a diameter DO of the outflow end 116 of the stent 102. In an embodiment, the diameters DI and DO may range between 18 and 30 mm in order to accommodate dimensions of the native valve anatomy. Stated another way, it may be desirable for the transcatheter valve prosthesis 100 to be available in varying size increments to accommodate varying diameters or sizes of a patient's native annulus. The stent 102 may be formed by a laser-cut manufacturing method and/or another conventional stent forming method as would be understood by one of ordinary skill in the art. The cross-section of the stent 102 may be circular, ellipsoidal, rectangular, hexagonal, square, trapezoidal, or other polygonal shape, although at present it is believed that circular, ellipsoidal, or trapezoidal may be preferable with the transcatheter valve prosthesis 100 being provided for replacement of an aortic valve. Similarly, the cross-section of the various struts that form the stent 102 may be circular, ellipsoidal, rectangular, hexagonal, square, trapezoidal, wedge-shaped, or other polygonal shape. The stent 102 has an expanded configuration, which is shown in the side view of FIG. 1C.

The inflow portion 108 is formed proximate to the inflow end 106 of the stent 102. The inflow portion 108 includes a plurality of crowns 110 and a plurality of struts 112 with each crown 110 being formed between a pair of opposing struts 112. Each crown 110 is a curved segment or bend extending between opposing struts 112. The inflow portion 108 is tubular, with a plurality of side openings 114 being defined by the plurality of crowns 110 and the plurality of struts 112. In an embodiment, the plurality of side openings 114 may be diamond-shaped. More particularly, as best shown in FIG. 1D, which is a side view of a single side opening 114 of the inflow portion 108 of the stent 102, each side opening 114 is formed by two pairs of opposing crowns 110 and four struts 112 therebetween. Each side opening 114 is symmetrical for easier integration with the prosthetic valve 132. A series of endmost inflow side openings 114A and a series of endmost inflow crowns 110A are formed at the inflow end 106 of the stent 102. The inflow end 106 of the stent 102, in some embodiments, has a total of twelve endmost inflow crowns 110A.

The outflow portion 118 may be formed proximate to the outflow end 116 of the stent 102. The outflow portion 118 includes a plurality of crowns 120 and a plurality of struts 122 with each crown 120 being formed between a pair of opposing struts 122. Each crown 120 is a curved segment or bend extending between opposing struts 122. The outflow portion 118 can be configured in a shape that forms a central lumen or passageway, for example, a ring. A series of endmost outflow crowns 120A are formed at the outflow end 116 of the stent 102. In some cases, the outflow end 116 of the stent 102 has a total of six endmost outflow crowns 120A. In an embodiment, the total of the endmost inflow crowns 110A is twice a total of the endmost outflow crowns 120A. In this embodiment, the endmost outflow crowns 120A are not connected to axial frame members 126 of the transition portion 124, but rather may be considered to be free or unattached while the remaining outflow crowns 120 of the outflow portion 118 are connected to the axial frame members 126 and disposed closer to the inflow end 106 than the endmost outflow crowns 120A.

The transition portion 124 bridges, connects, or otherwise extends between the inflow portion 108 and the outflow portion 118. While the stent 102 has been described as including a transition portion 124, one skilled in the art will realize that the transition portion 124 may form a portion of the inflow portion 108 and/or the outflow portion 118; for example, the embodiments of FIGS. 3-13 are described with the transition portion (equivalent to transition portion 124 of FIG. 1) and the outflow portion (equivalent to outflow portion 118 of FIG. 1) as collectively being part of the outflow portion. In some instances, the transition portion 124 includes a total of six axial frame members 126, each axial frame member 126 extending between a crown 120 of the outflow portion 118 and a crown 110 of the inflow portion 108. More particularly, each axial frame member 126 is an axial segment having a first end 128 connected to a crown 120 of the outflow portion 118 and a second end 130 connected to a crown 110 of the inflow portion 108. The axial frame members 126 are substantially parallel to the central longitudinal axis of the stent 102. Each axial frame member 126 is disposed approximately halfway between a pair of adjacent endmost outflow crowns 120A. Three of the six axial frame members 126 are commissure posts 126A and aligned with and attached to a respective commissure of the three leaflets 134 of the prosthetic valve 132. Three of the axial frame members 126 are axial struts 126B and are disposed between adjacent commissure posts 126A. The axial frame members 126 aid in valve alignment and coaptation. More particularly, the axial frame members 126 reinforce or strengthen the commissure region of the prosthetic valve 132 by shaping the leaflets 134 and supporting the leaflets 134 during opening and closing thereof, and thus provide more reliable leaflet coaptation. Symmetrical cell expansion ensures that stent 102 crimps well onto a balloon of a balloon catheter for delivery. Poor crimp quality may lead to portions of the stent 102 overlapping when crimped, which in turn may cause tissue damage to the valve leaflets of the prosthetic valve during the crimping process.

The prosthetic valve 132 is disposed within and secured to at least the transition portion 124 of the stent 102 at the commissure posts 126. In addition, the prosthetic valve 132 may also be disposed within and secured to the inflow portion 108 of the stent 102.

In the embodiment shown, there is a single row of struts 122 and crowns 120 between the first ends 128 and the outflow end 116 of the stent 102. Further, in the embodiment shown, exactly two struts 122 and a single crown 120 of the outflow portion 118 are disposed between adjacent axial frame members 126. Such an arrangement provides a series of six endmost outflow side openings or cells 125 formed at the outflow portion 118 of the stent 102. Each endmost outflow side opening or cell 125 defines an open space in the stent 102, which is formed in any type of shape, in the radially expanded configuration. In an embodiment, as best shown in FIG. 1E, which is a side view of a single endmost outflow side opening 125 of the stent 102, each endmost outflow side opening 125 is defined by two adjacent struts 122 of the outflow portion 118, four adjacent struts 112 of the inflow portion 108, and two adjacent axial frame members 126 of the transition portion 124. The endmost outflow side openings 125 of the outflow portion 118 are relatively larger than the plurality of side openings 114 of the inflow portion 108 (defined by four adjacent struts 112 of the inflow portion 108, as best shown in FIG. 1D) to improve access to the coronary arteries. More particularly, the endmost outflow side openings 125 of the outflow portion 118 are configured to be of sufficient size to be easily crossed with a coronary guide catheter into either the right coronary artery or the left main coronary artery once the transcatheter valve prosthesis 100 is deployed in situ. The inflow portion 108 includes exactly three rows of struts 112 and crowns 110 between the second ends 130 of the axial frame members 126 and the inflow end 106 of the stent 102. Further, four struts 112 and three crowns 110 are disposed between the second ends 130 of adjacent axial frame members 126.

The length or height of the inflow portion 108 may vary from that depicted herein in order to accommodate dimensions of the native valve anatomy. For example, in another embodiment as shown in FIG. 2, a transcatheter valve prosthesis 200 is shown that is relatively longer than the transcatheter valve prosthesis 100 of FIG. 1.

FIG. 2 is a schematic diagram illustrating a side view of another non-limiting example 200 of a transcatheter valve prosthesis in an expanded configuration, in accordance with various embodiments.

More particularly, the transcatheter valve prosthesis 200 includes a stent or frame 202 (hereinafter referred to simply as "stent 202") having graft material 244 which encloses or lines a portion of the stent 202 as would be known to one of ordinary skill in the art of prosthetic tissue valve construction. The stent 202 is a tubular component that defines an inflow end 206 and an outflow end 216 of the transcatheter valve prosthesis 200. An inflow portion 208 of the stent 202 is relatively longer than the inflow portion 108 of the stent 102 so that the overall length or height of the transcatheter valve prosthesis 200 may be relatively increased or decreased to accommodate dimensions of the native valve anatomy. For example, a height or length of the stent 202 in the expanded configuration may be between 18 and 24 mm. The transcatheter valve prosthesis 200 of FIG. 2 would otherwise be similar, if not identical, to transcatheter valve prosthesis 100 of FIG. 1.

Figure 3:
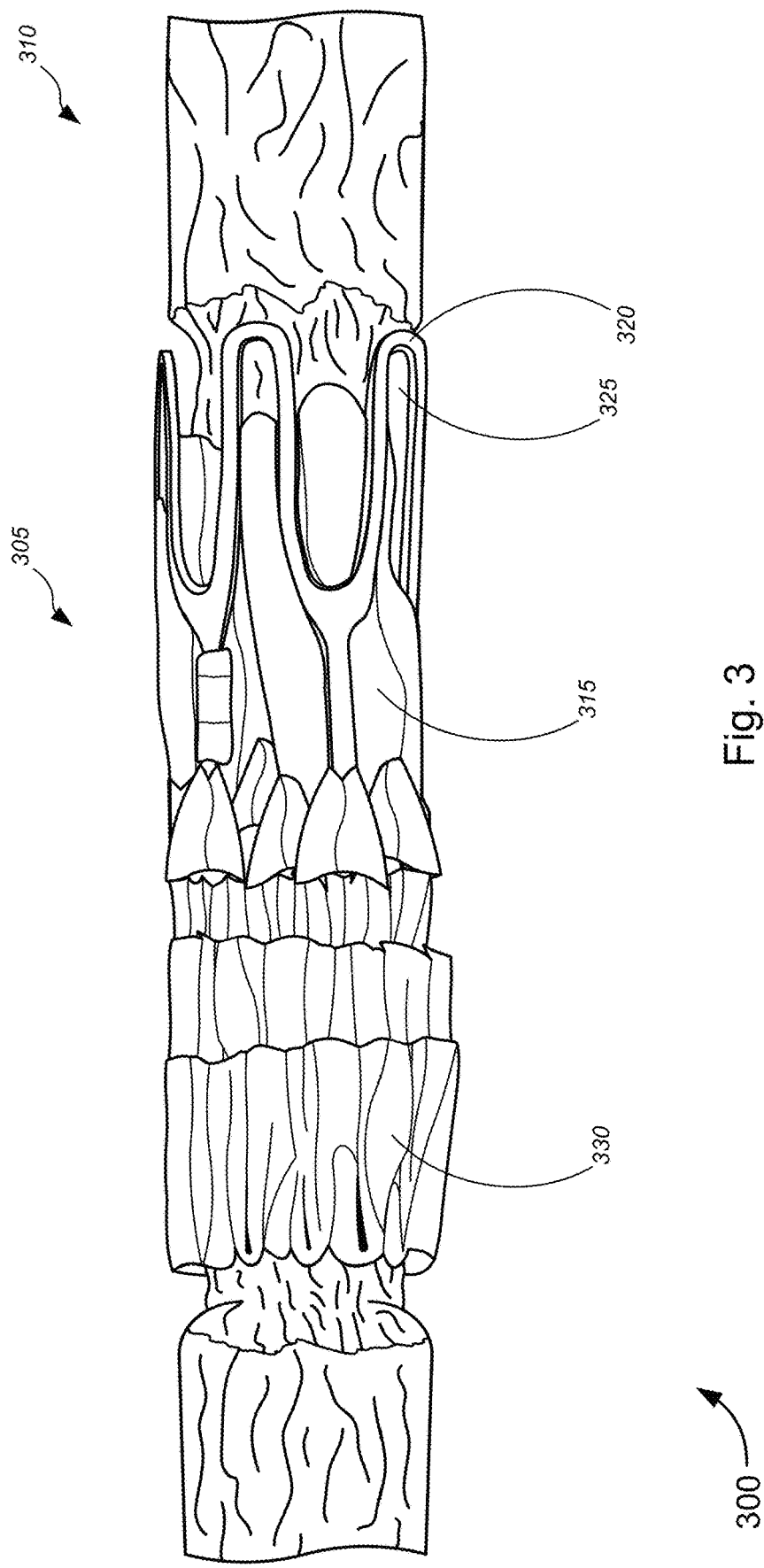
FIG. 3 is a diagram illustrating a system for delivery of a medical device to be implanted within a body of a subject, in accordance with various embodiments.

FIG. 3 is a diagram illustrating a system 300 for delivery of a medical device to be implanted within a body of a subject, in accordance with various embodiments.

Referring to the non-limiting embodiment of FIG. 3, system or assembly 300 may comprise a medical device 305 (in this case, a transcatheter valve prosthesis not unlike transcatheter valve prostheses 100 or 200 of FIG. 1 or 2, or the like; although the various embodiments are not limited to the medical device being a transcatheter valve prosthesis) and a delivery system 310 (in this case, a catheter-based or balloon-based delivery system, or the like; although the various embodiments are not limited to the delivery system being a delivery system balloon). The medical device 305 may include, without limitation, at least one tissue layer 315 (which, in some cases, might correspond to prosthetic valve 132 of FIG. 1, or the like) and a stent or frame 320 (formed by a plurality of struts and, in some cases, a plurality of crowns and/or a plurality of axial frame members, or the like; which, in some cases, might correspond to stent 102 of FIG. 1, or the like). The stent or frame 320 may include a plurality of openings or cells that are defined at least in part by two or more struts among the plurality of struts (and, in some cases, also by one or more crowns among the plurality of crowns and/or by one or more axial frame members among the plurality of axial frame members, and/or the like). In some instances, the stent or frame 320 may further include an inflow portion (similar to inflow portion 108 of FIG. 1, or the like) and an outflow portion (similar to the combination of outflow portion 118 and transition portion 124 of FIG. 1, or the like), with the inflow portion being substantially covered by at least an outer skirt 330 (and, in some cases, also by an inner skirt (not shown in FIG. 3)). Outflow openings 325, which are not covered by a skirt (whether outer or inner skirt), may present a pinch risk during crimping of the medical device 305 for delivery to an implantation site (e.g., a native heart valve, or other suitable implantation site, or the like) in a body of a subject, due to its design, particularly if the outflow openings 325 defined at least in part by the two or more struts (and, in some cases, the one or more crowns and/or the one or more axial frame members, and/or the like) in the outflow portion of the stent or frame 320 is substantially larger than the inflow openings defined by corresponding struts (and, in some cases, crowns) in the inflow portion of the stent or frame 320.

In a non-limiting example, during balloon expandable transcatheter aortic valve replacement ("TAVR"), the preparation of a sample may involve crimping an implant onto a delivery system balloon. Certain features on the implant—including, without limitation, large outflow frame cells or openings, wide leaflets, long leaflets, and/or the like—and/or certain procedural effects—including, but not limited to, high crimp forces, or the like—may make some designs more susceptible to leaflet pinching. Leaflet pinching refers to a situation in which one or more leaflets become caught between two or more struts (and/or crowns or axial frame members, and/or the like) as the implant is crimped to its final profile. The immediate effect seen is leaflet peeling and cuts. The damage produced from this action can cause long term durability issues for the implant and valve.

To mitigate the occurrences of leaflet pinching, a leaflet protection tool or, more generally, an implant tissue protection tool (such as described below with respect to FIGS. 4-15, or the like) may be used during crimping of the medical device.

FIGS. 4-11B are diagrams illustrating various non-limiting examples of an implant tissue protection tool that may be used to protect at least one tissue layer of a medical device during crimping of the medical device prior to implantation of the medical device within a body of a subject, in accordance with various embodiments.

In various embodiments, such as shown in FIGS. 4-11B or the like, an implant tissue may comprise an outer portion and at least one protrusion affixed to a first surface of the outer portion. The outer portion may be configured to surround one or more outer segments of at least one tissue layer of a medical device to be implanted into a body of a subject. The at least one protrusion may be configured to minimize (and, in some cases, prevent) occurrence (or likelihood of occurrence) of the at least one tissue layer of the medical device passing through at least one opening defined at least in part by two or more struts of the medical device during crimping of the medical device by a crimping device in preparation for implantation into the body of the subject. That is, the at least one protrusion may be configured to actively push radially inward against the at least one tissue layer of the medical device to minimize (and, in some cases, prevent) pinching of the at least one tissue layer by two or more struts (or other stent or frame structure) of the medical device while the medical device is being crimped in preparation for delivery of the medical device to an implantation site within the body of the subject. The implant tissue protection tool described herein is separate from, and has a structure as a whole that is independent of, the crimping device.

In the embodiments in which the medical device is a transcatheter valve prosthesis or the like (such as transcatheter valve prosthesis 100 of FIG. 1, or the like), the at least one tissue layer might include a prosthetic valve or the like (such as prosthetic valve 132 of FIG. 1, or the like), which may include leaflets or leaflet structures that are susceptible to pinching during crimping, especially for medical devices that have certain features (including, but not limited to, large outflow frame cells or openings, wide leaflets, long leaflets, and/or the like) and/or are subject to certain procedural effects (including, without limitation, high crimp forces, or the like). According to some embodiments, an area of each outflow cell or opening may be greater than an area of each inflow cell or opening by a ratio of at least 1.5:1 (in some cases, at least 2:1, at least 3:1, at least 4:1, or more). In some instances, the outflow portion may further include 6 outflow cells or openings per row, while the inflow portion may further include 12 inflow cells or openings per row. Alternatively, any suitable number of cells or openings for the inflow and outflow portions may be used with the number of inflow cells or openings per row being the same or greater than the number of outflow cells or openings per row (not limited to 12 and 6, respectively).

In some embodiments, the outer portion may comprise a sleeve that is configured to fit snugly over an outer perimeter of the medical device, where the at least one protrusion may be configured to extend radially inward through the at least one opening that is not covered by a skirt layer of the medical device (as shown, e.g., in FIGS. 4-8B, or the like). Although not shown in the figures, a single protrusion may be configured to extend radially inward through one or more openings that are not covered by a skirt layer of the medical device to minimize occurrence of two or more leaflets passing through said one or more openings during crimping. For maximum effectiveness of the design, the implant tissue protection tool may include at least one protrusion per each opening that may be configured to contact the at least one tissue layer of the medical device (e.g., leaflets, etc.). In some cases, the sleeve may have a longitudinal length that covers at least a portion of a longitudinal length of the medical device, the longitudinal length of the sleeve being configured to at least partially cover all openings defined at least in part by struts of the medical device that are not covered by the skirt layer (as shown, e.g., in FIGS. 4-7, or the like).

According to some embodiments, the at least one protrusion may comprise a plurality of protrusions affixed to the inner surface of the sleeve, where at least one protrusion among the plurality of protrusions may be configured to extend through each opening defined at least in part by struts of the medical device that are not covered by the skirt layer (as shown, e.g., in FIGS. 4-8B, or the like). In some instances, the at least one protrusion among the plurality of protrusions that may be configured to extend through each opening defined at least in part by the struts of the medical device that are not covered by the skirt layer may comprise two protrusions that are configured to extend through each opening (as shown, e.g., in FIG. 7, or the like). In some cases, each of the plurality of protrusions may have a length that is similar to a longitudinal length of the sleeve, wherein the length of each protrusion may be aligned with the longitudinal length of the sleeve when each of the plurality of protrusions is affixed to the sleeve, and wherein the length of each of the at least one protrusion may be configured to fit within each of the openings defined at least in part by struts of the medical device that are not covered by the skirt layer (as shown, e.g., in FIGS. 4-8B, or the like).

In some embodiments, the implant tissue protection tool may be selectable from among a plurality of versions of the implant tissue protection tool, each version having a different combination of depth and thickness of each of the at least one protrusion. As described herein, the depth of each protrusion extends radially inward, while the thickness extends in a direction parallel to a tangent from the outer portion. The implant tissue protection tool may be selectable with appropriate depth and thickness of each of the at least one protrusion to minimize (and, in some cases, prevent) occurrence of the at least one tissue layer of the medical device passing through the at least one opening during crimping of the medical device.

Figure 4:
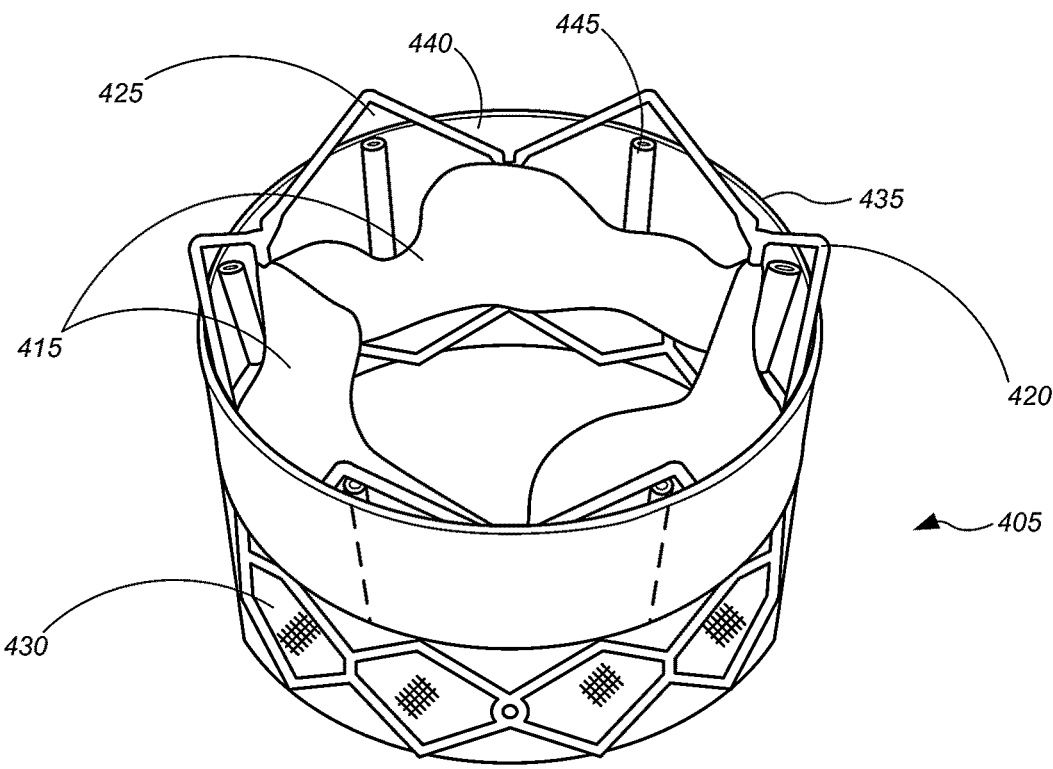
FIGS. 4-11B are diagrams illustrating various non-limiting examples of an implant tissue protection tool that may be used to protect at least one tissue layer of a medical device during crimping of the medical device prior to implantation of the medical device within a body of a subject, in accordance with various embodiments.

Merely by way of example, in some cases, each of the at least one protrusion may have a hollow cylindrical shape (as shown, e.g., in FIG. 4, or the like). Alternatively, each of the at least one protrusion may have a wrapped cylindrical shape (as shown, e.g., in FIG. 5, or the like). Alternatively, each of the at least one protrusion may have a flared hollow polygonal prism shape (as shown, e.g., in FIGS. 6A and 6B, or the like). Alternatively, each of the at least one protrusion may have a hollow flattened cylindrical shape (as shown, e.g., in FIG. 7, or the like).

According to some embodiments, the at least one protrusion may comprise a plurality of protrusions, where the outer portion and the plurality of protrusions may be integrally formed as a flat continuous band and where the plurality of protrusions may each be formed by folding the flat continuous band in on itself, with the outer portion being configured to wrap around an outer perimeter of the medical device and with at least one protrusion among the plurality of protrusions being configured to extend through each of the at least one opening that is not covered by a skirt layer (as shown, e.g., in FIG. 4, or the like).

In some embodiments, the at least one protrusion may comprise a plurality of protrusions, where the outer portion and the plurality of protrusions may be integrally formed using a pliable material (as shown, e.g., in FIGS. 8A, 8B, 10A, and 10B, or the like). In some instances, the implant tissue protection tool may be configured to wrap around the outer perimeter of the medical device, with the plurality of protrusions each being configured to extend through the at least one opening that is not covered by a skirt layer (as shown, e.g., in FIGS. 8A and 8B, or the like). Alternatively, the implant tissue protection tool may be configured to be wedged between the one or more outer segments of the at least one tissue layer and the two or more struts of the medical device, with the plurality of protrusions each being configured to extend along a direction that is either parallel with or at a small angle with respect to an axis of the medical device, where the integrally formed outer portion and plurality of protrusions may be configured to be disposed between the one or more outer segments of the at least one tissue layer and the two or more struts of the medical device, without the plurality of protrusions extending longitudinally beyond a longitudinal length of the medical device when fully wedged between the one or more outer segments of the at least one tissue layer and the two or more struts of the medical device (as shown, e.g., in FIGS. 10A and 10B, or the like).

Figure 11A:
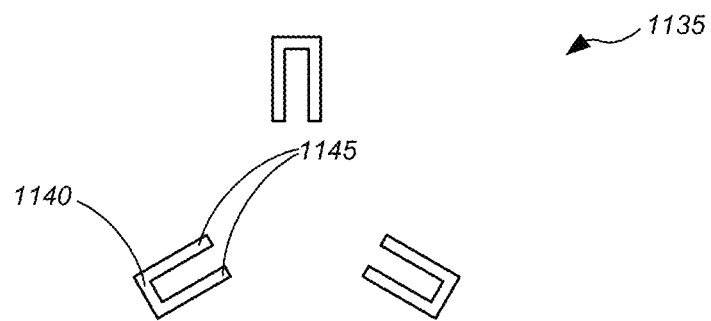
Figure 11B:
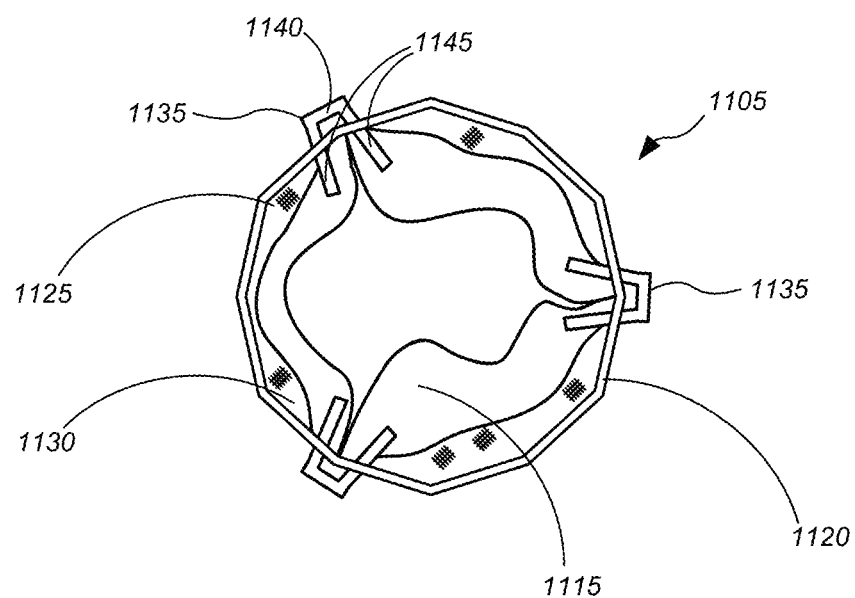

According to some embodiments, the implant tissue protection tool may further comprise a plurality of clips, each clip including a connecting portion forming part of the outer portion, where the at least one protrusion may comprise at least two protrusions extending from each connecting portion of each clip (as shown, e.g., in FIGS. 11A and 11B, or the like). In some cases, the plurality of clips may be connected together along the connecting portions.

In some embodiments, the implant tissue protection tool may be made of a material that is the same as a material from which the at least one tissue layer is made, where such tissue layer material may include, but is not limited to, at least one of animal tissue, bovine pericardium, porcine pericardium, fabric, or expanded polytetrafluoroethylene ("ePTFE"), and/or the like. Alternatively, or additionally, the implant tissue protection tool may be made of a material comprising at least one of animal tissue, bovine pericardium, porcine pericardium, open-cell foam, polyurethane foam, fabric, or expanded polytetrafluoroethylene ("ePTFE"), and/or the like.

According to some embodiments, crimping of the medical device may comprise a partial crimp that reduces a first diameter of the medical device to a second diameter smaller than the first diameter and a final crimp that reduces the second diameter of the medical device to a third diameter smaller than the second diameter. The implant tissue protection tool may be separated from the medical device after the partial crimp and before the final crimp. In some cases, the medical device may be pre-packaged with the implant tissue protection tool already being removably affixed to the medical device. Alternatively, the medical device and the implant tissue protection tool may be packaged separately, for later attachment by a healthcare professional or third party agent.

We now turn to the specific, non-limiting examples shown in FIGS. 4-11B.

FIG. 4 depicts a non-limiting example 400 of an assembly comprising a medical device 405 (in this case, a transcatheter valve prosthesis similar to transcatheter valve prosthesis 100 of FIG. 1, or the like) and an implant tissue protection tool 435 (in this case, a leaflet protection tool, or the like).

The medical device 405 may include, without limitation, at least one tissue layer 415 (in this case, a prosthetic valve similar to prosthetic valve 132 of FIG. 1, or the like, which may include one or more leaflets or leaflet structures, or the like) and a stent or frame 420 (similar to stent 102 of FIG. 1, or the like, which may include a plurality of struts, a plurality of crowns, and/or a plurality of axial frame members, and/or the like). The stent or frame 420 may include a plurality of openings or cells that are defined at least in part by two or more struts among the plurality of struts (and, in some cases, also by one or more crowns among the plurality of crowns and/or by one or more axial frame members among the plurality of axial frame members, and/or the like). In some instances, the stent or frame 420 may further include an inflow portion (similar to inflow portion 108 of FIG. 1, or the like) and an outflow portion (similar to the combination of outflow portion 118 and transition portion 124 of FIG. 1, or the like), with the inflow portion being substantially covered by at least an outer skirt 430 (and, in some cases, also by an inner skirt (not shown in FIG. 4) or an inner skirt instead of an outer skirt (also not shown in FIG. 4)). Outflow openings 425, which are not covered by a skirt (whether outer or inner skirt), may present a pinch risk during crimping of the medical device 405 for delivery to an implantation site (e.g., a native heart valve, or other suitable implantation site, or the like) in a body of a subject, due to its design, particularly if the outflow openings 425 defined at least in part by the two or more struts (and, in some cases, the one or more crowns and/or the one or more axial frame members, and/or the like) in the outflow portion of the stent or frame 420 is substantially larger than the inflow openings defined by corresponding struts (and, in some cases, crowns) in the inflow portion of the stent or frame 420.

The implant tissue protection tool 435 may include, but is not limited to, an outer portion 440 and at least one protrusion 445 affixed to a first surface of the outer portion 440 (in some cases, integrally formed from the outer portion, or the like). The outer portion 440 may be configured to surround one or more outer segments of the at least one tissue layer 415 of the medical device 405 to be implanted into the body of the subject. The at least one protrusion 445 may be configured to minimize (and, in some cases, prevent) occurrence (or likelihood of occurrence) of the at least one tissue layer 415 of the medical device 405 passing through at least one opening 425 defined during crimping of the medical device 405 by a crimping device (such as shown in FIG. 13B, or the like) in preparation for implantation into the body of the subject. That is, the at least one protrusion 445 may be configured to actively push radially inward against the at least one tissue layer 415 of the medical device 405 to minimize (and, in some cases, prevent) pinching of the at least one tissue layer 415 by two or more struts (or other stent or frame structure) 420 of the medical device 405 while the medical device 405 is being crimped in preparation for delivery of the medical device 405 to an implantation site within the body of the subject. The implant tissue protection tool 435 described herein is separate from, and has a structure as a whole that is independent of, the crimping device.

In some embodiments, the implant tissue protection tool 435 may be placed over the outflow cells or openings 425 to centrally align with the outflow cells or openings 425. The at least one protrusion 445 (referred to herein also as "petals" or the like) may push the leaflet material 415 in toward the delivery system (similar to delivery system 310 in FIG. 3, or the like), away from the frame or stent 420. The depth of the protrusions (or petals) 445 may be varied to help deflect leaflets 415 inwards. In some cases, the protrusions (or petals) 445 may be assembled, configured, or constructed to have a predetermined depth designed to deflect leaflets of particular prosthetic valves.

FIGS. 5-11B depicts assemblies and their component medical devices and implant tissue protection tools each comprising similar components as those of the corresponding components of FIG. 4, and similar reference numerals (particularly the last two digits of the reference numerals) denote similar components. For example, medical device 405 (and components 415-430) corresponds to each of medical device 505 (and components 515-530), medical device 605 (and components 615-630), medical device 705 (and components 715-730), medical device 805 (and components 815-830), medical device 905 (and components 915-930), medical device 1005 (and components 1015-1030), and medical device 1105 (and components 1115-1130). Similarly, implant tissue protection tool 435 (and components 440 and 445) corresponds to each of implant tissue protection tool 535 (and components 540 and 545), implant tissue protection tool 635 (and components 640 and 645), implant tissue protection tool 735 (and components 740 and 745), implant tissue protection tool 835 (and components 840 and 845), implant tissue protection tool 935 (and component 940), implant tissue protection tool 1035 (and components 1040 and 1045), and implant tissue protection tool 1135 (and components 1140 and 1145). Accordingly, unless otherwise indicated below, the description of medical device 405 (and components 415-430) and implant tissue protection tool 435 (and components 440 and 445) would similarly apply to the corresponding components of medical devices 505, 605, 705, 805, 905, 1005, and 1105 (and their corresponding components) and implant tissue protection tools 535, 635, 735, 835, 935, 1335, and 1135 (and their corresponding components).

Figure 5:
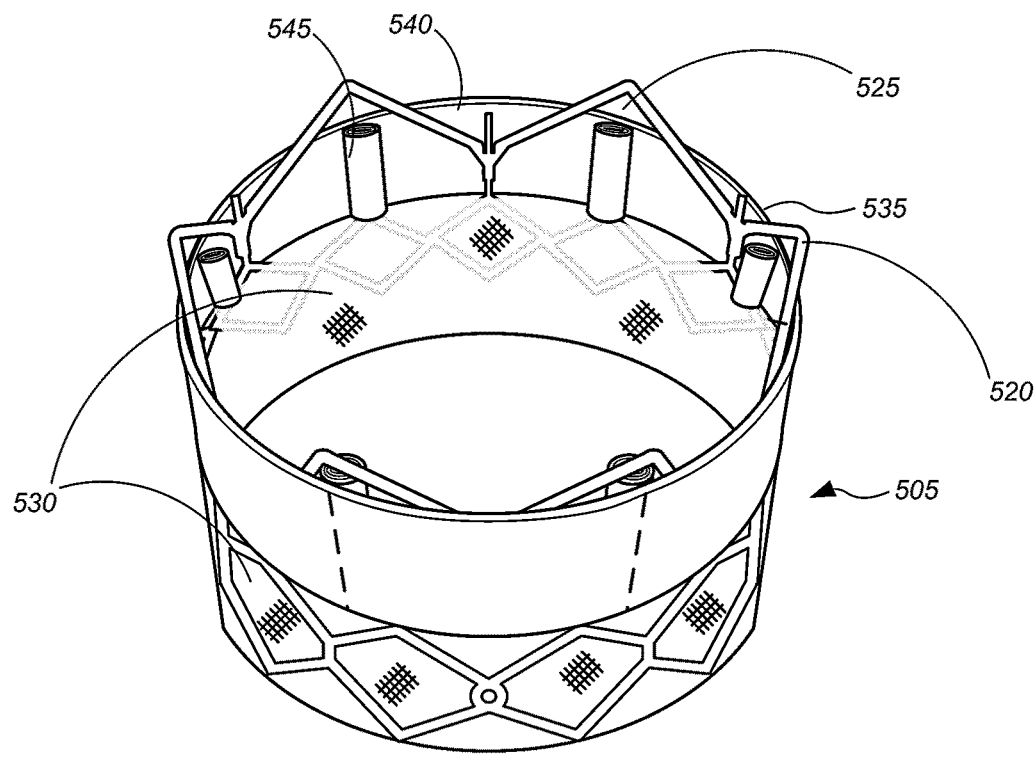

With reference to the non-limiting embodiment 500 of FIG. 5, the implant tissue protection tool 535 may be placed over the outflow cells or openings 525 to centrally align with the outflow cells or openings 525. The at least one protrusion (or petals) 545 may push the leaflet material 515 in toward the delivery system (similar to delivery system 310 in FIG. 3, or the like), away from the frame or stent 520. The depth of the protrusions (or petals) 545 may be varied to help deflect leaflets 515 inwards. In some cases, the protrusions (or petals) 545 may be assembled, configured, or constructed to have a predetermined depth designed to deflect leaflets of particular prosthetic valves. The thicker profile with additional material in the center of each protrusion (or petal) 545—in some cases, foam or wrapped protrusion material, or the like—may add compressibility and may increase surface area coverage of outflow cell or opening 525.

Figure 6A:
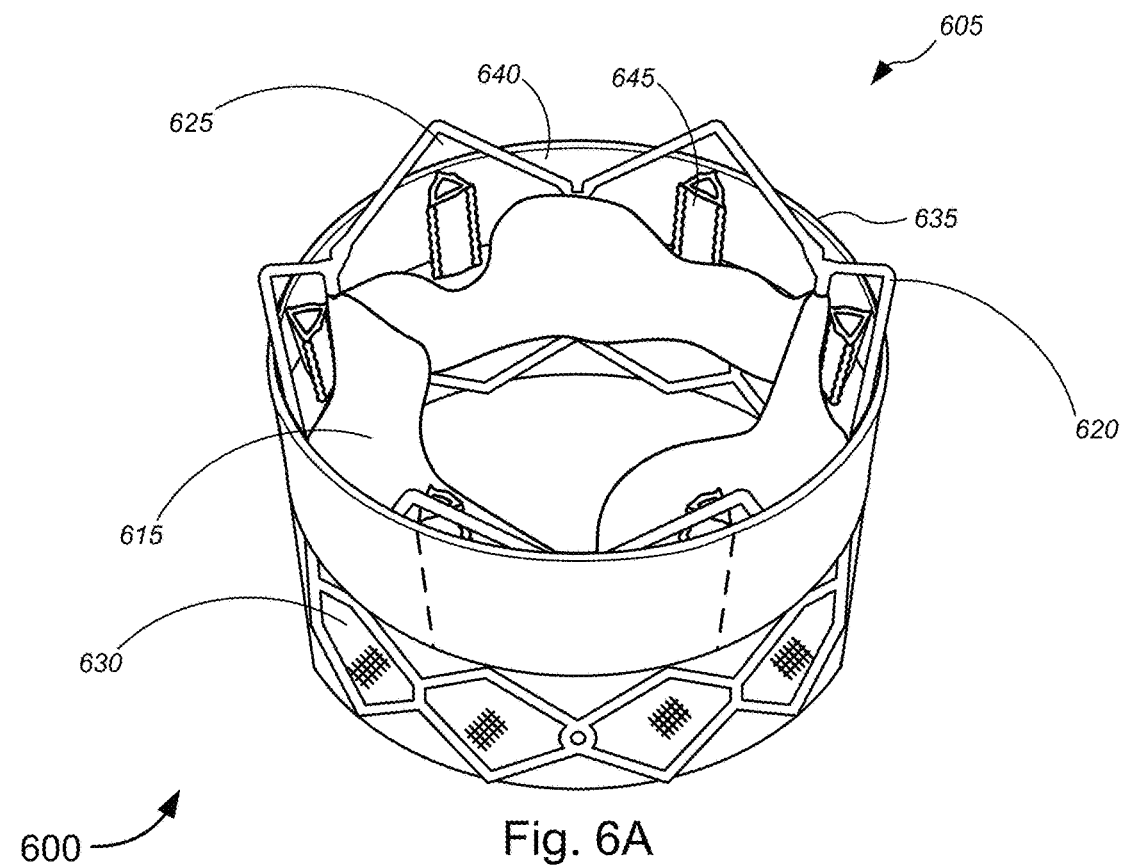
Figure 6B:
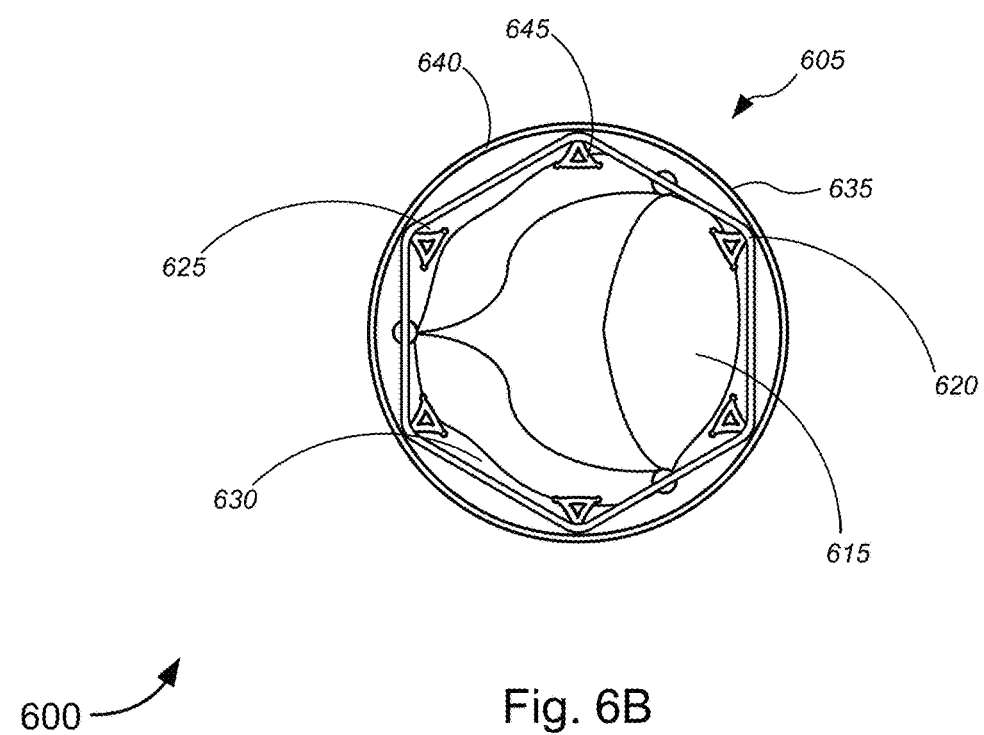

Turning to the non-limiting embodiment 600 of FIGS. 6A and 6B (collectively, "FIG. 6"), the implant tissue protection tool 635 may be placed over the outflow cells or openings 625 to centrally align with the outflow cells or openings 625. The at least one protrusion (or petals) 645 may push the leaflet material 615 in toward the delivery system (similar to delivery system 310 in FIG. 3, or the like), away from the frame or stent 620. The depth and width of the protrusions (or petals) 645 may be varied to help deflect leaflets 615 inwards as well as to block a larger area of the outflow cell or opening 625. In some cases, the protrusions (or petals) 645 may be assembled, configured, or constructed to have a predetermined depth and a predetermined width designed to deflect leaflets of particular prosthetic valves. With reference to FIGS. 5 and 6, where protrusions 545 each has a general rolled or cylindrical shape with one side of the rolled or cylindrical shape of each protrusion being affixed to (or extending from) the inner/first surface of the outer portion 540 of the implant tissue protection tool 535, protrusions 645 each has a general triangular prism or convex-sided triangular prism shape with crimped edges along the corners of the triangular profile and with one such corner being affixed to (or extending from) the inner/first surface of the outer portion 640 of the implant tissue protection tool 635. In some cases, the protrusions 545 may include additional material in the center of each protrusion (or petal) 545, whereas the protrusions 645 may be hollow at the center of each protrusion (or petal) 645. The flared shape of each protrusion (or petal) 645 may increase surface area coverage of outflow cell or opening 625.

Figure 7:
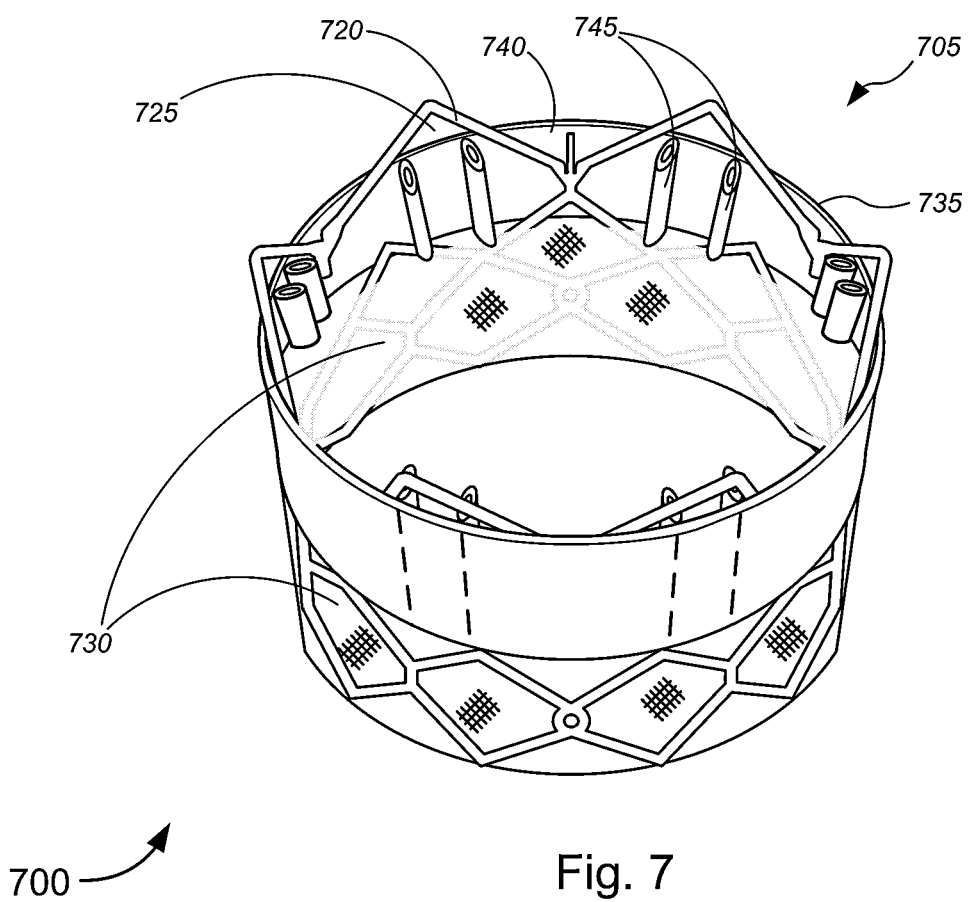

Referring to the non-limiting embodiment 700 of FIG. 7, the implant tissue protection tool 735 may be placed over the outflow cells or openings 725 to centrally align with the outflow cells or openings 725. Two protrusions (or petals) 745 may be aligned within each outflow cell or opening 725 symmetrically, and may push the leaflet material 715 in toward the delivery system (similar to delivery system 310 in FIG. 3, or the like), away from the frame or stent 720. The depth of the protrusions (or petals) 745 may be varied to help deflect leaflets 715 inwards. In some cases, the protrusions (or petals) 745 may be assembled, configured, or constructed to have a predetermined depth to deflect leaflets of particular prosthetic valves. The double protrusions (or petals) 745 serve to provide more area coverage of outflow cell or opening 725, i.e., to cover more area to block the leaflets 715 from the frame struts 720.

Figure 8A:
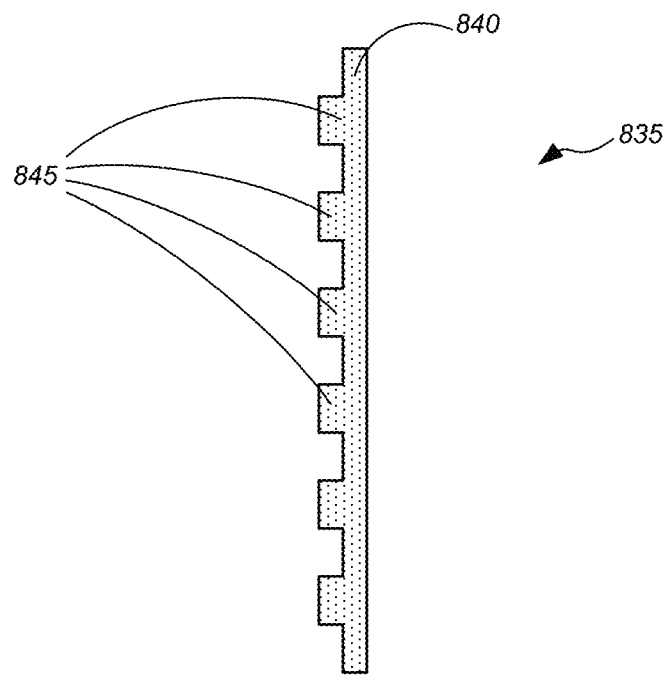
Figure 8B:
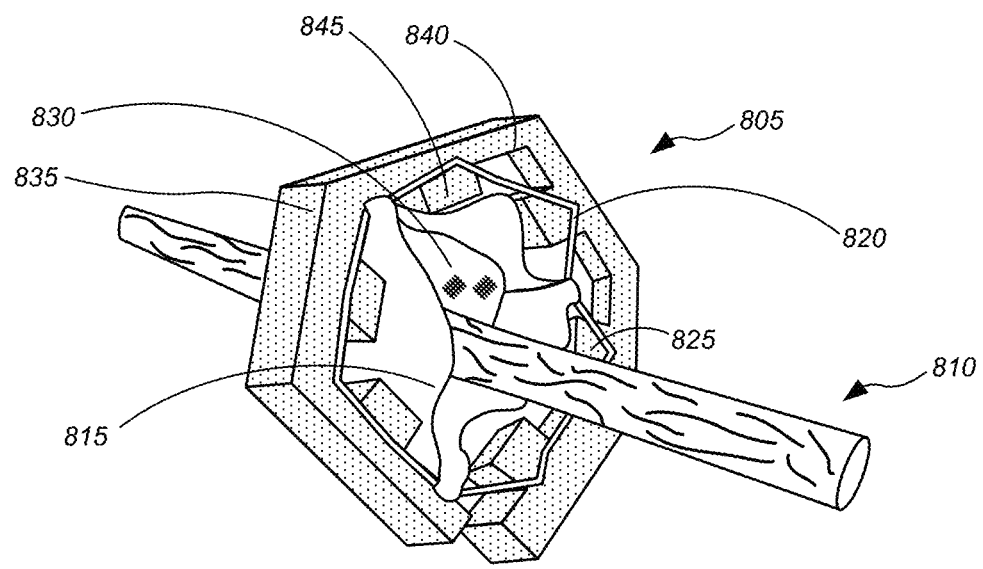

With reference to the non-limiting embodiment 800 of FIGS. 8A and 8B (collectively, "FIG. 8"), the implant tissue protection tool 835 may be placed over the outflow cells or openings 825 to centrally align with the outflow cells or openings 825. The at least one protrusion (or protruding feature) 845 may each cover the entire outflow cell or opening 725, and thus may push the leaflet material 815 in toward the delivery system (similar to delivery system 310 in FIG. 3, or the like), away from the frame or stent 820. The material may be compressible, but may keep its structure, and the implant tissue protection tool 835 may be open ended (as shown, e.g., in FIG. 8A) for easier removal.

Figure 9A:
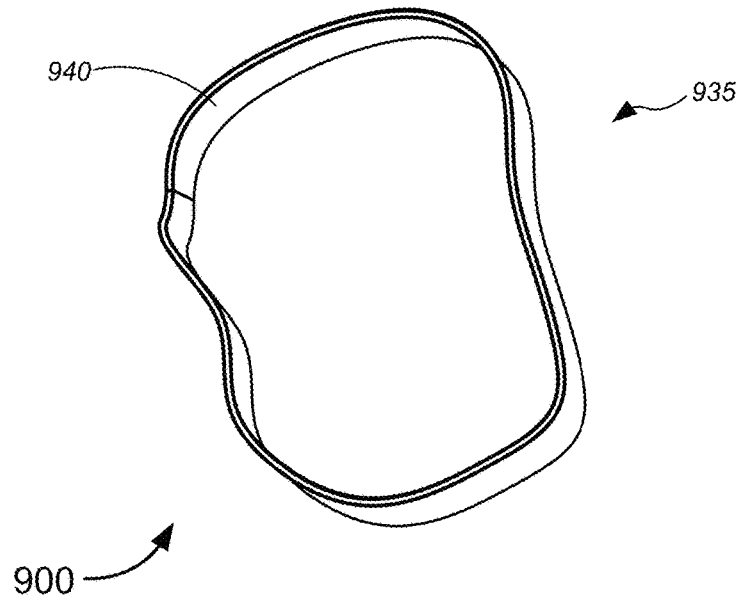
Figure 9B:
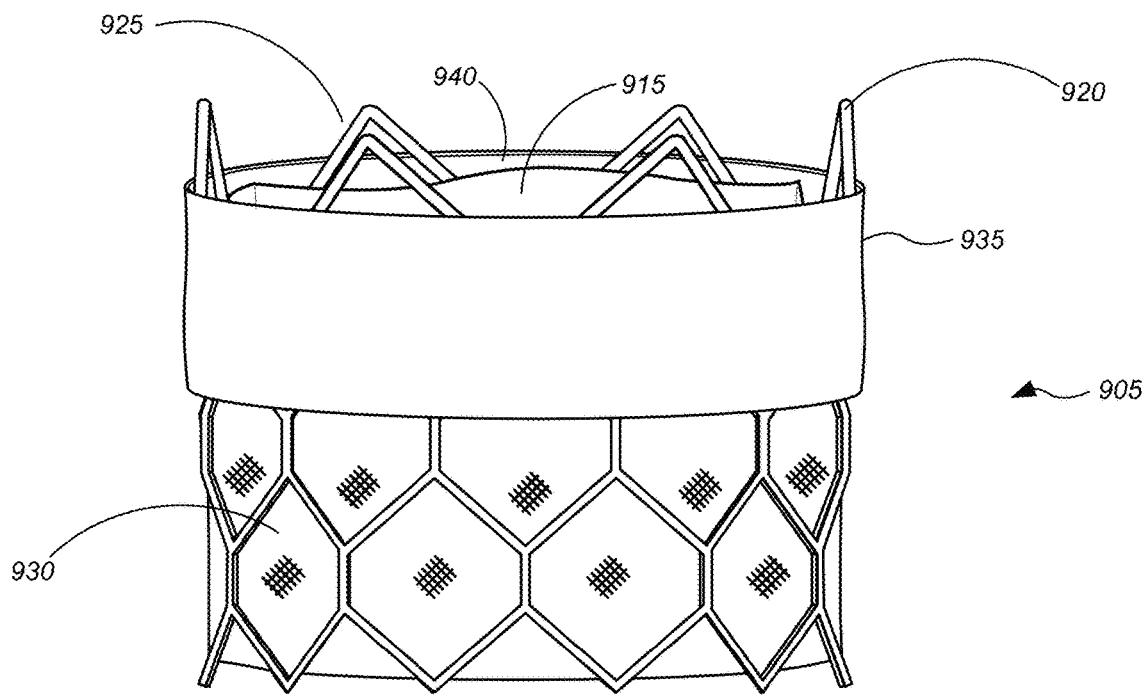

Turning to the non-limiting embodiment 900 of FIGS. 9A and 9B (collectively, "FIG. 9"), the implant tissue protection tool 935 may be placed over the outflow cells or openings 925 to centrally align with the outflow cells or openings 925. The implant tissue protection tool 935 may fit over the outflow cells or openings 925. During crimping, the implant tissue protection tool 935 may fold and wave in and out of the outflow cells or openings 725 to serve as a way to push the leaflet material 915 in toward the delivery system (similar to delivery system 310 in FIG. 3, or the like), away from the frame or stent 920.

Figure 10A:
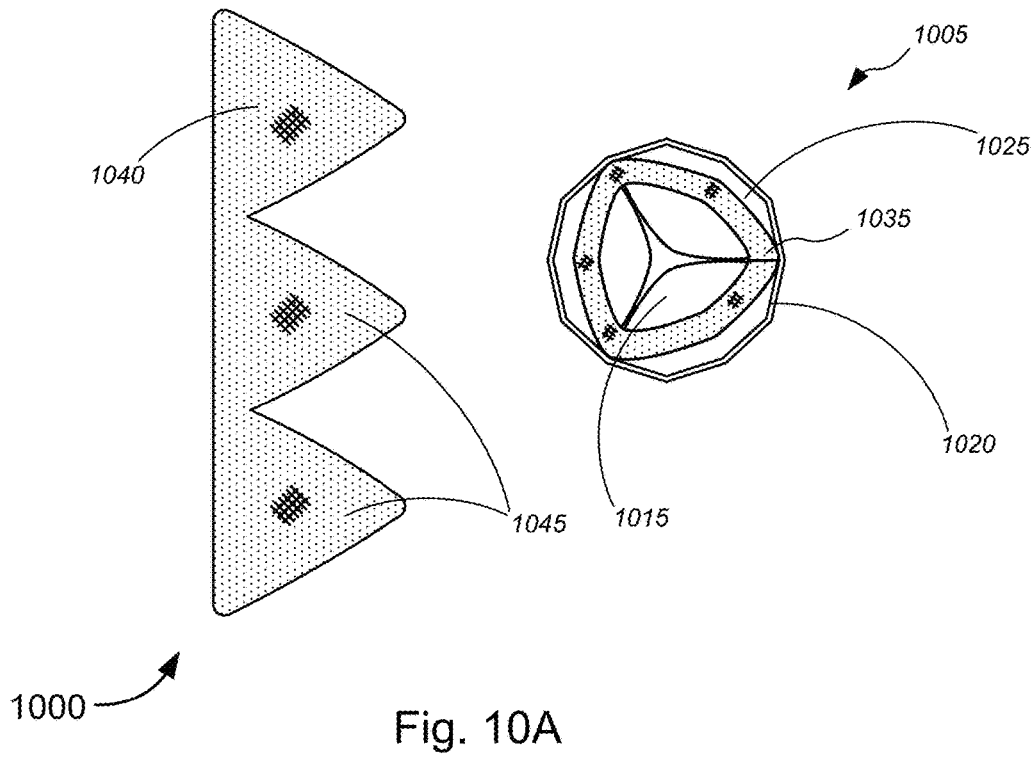
Figure 10B:
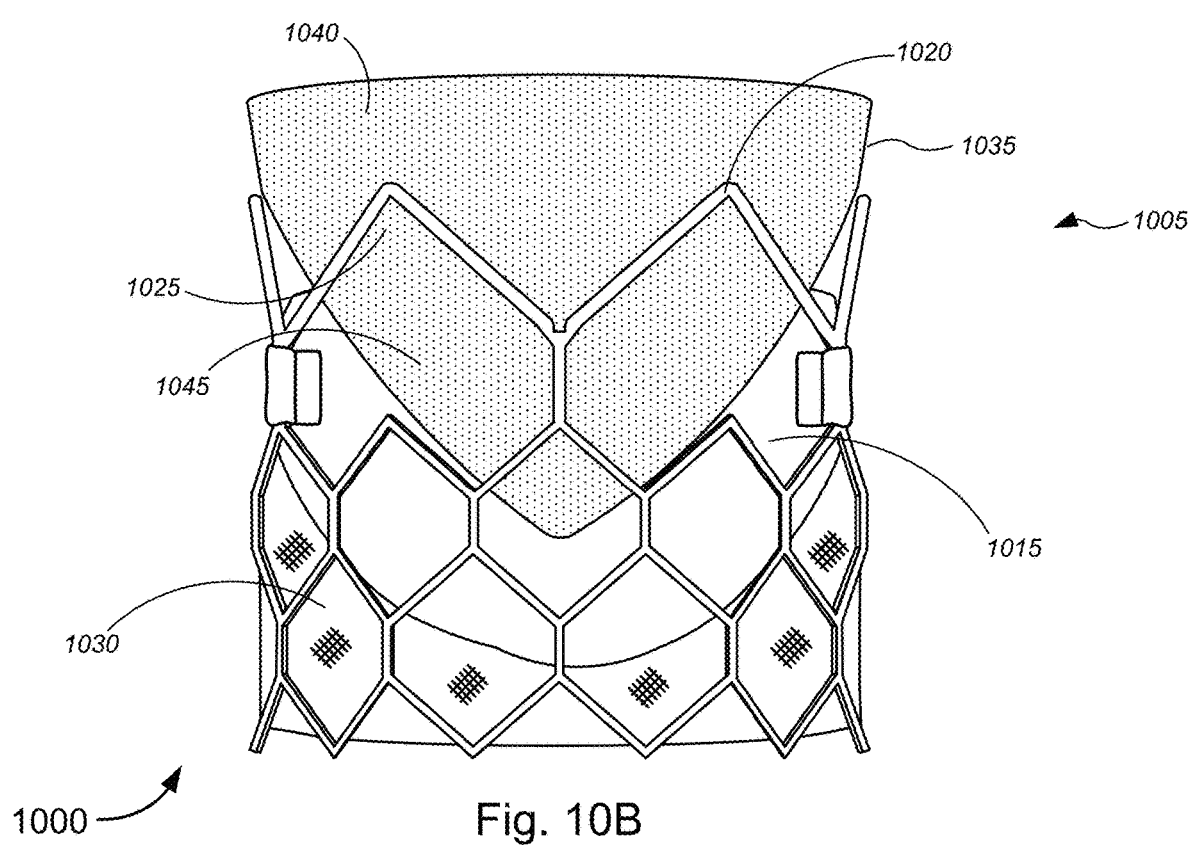

Referring to the non-limiting embodiment 1000 of FIGS. 10A and 10B (collectively, "FIG. 10"), the implant tissue protection tool 1035 may be wedged between the leaflets 1015 and the frame 1020, and may block the entire outflow cell or opening 1025 by keeping entire leaflets 1015 pushed inward during crimping. The implant tissue protection tool 1035 may be removed from the proximal end of the implant (i.e., outflow end) and wriggled out from under the crimped (or partially crimped) implant or medical device 1005.

With reference to the non-limiting embodiment 1100 of FIGS. 11A and 11B (collectively, "FIG. 11"), the implant tissue protection tool 1135 (also referred to herein as "clips" or the like) may comprise 3 or more separate pieces or separate pieces that may be connected together. The clips 1135 may vary in protruding depth (i.e., length of protrusions or "clip legs" 1145) and fit over commissure bars of the medical device 1105. The clip legs 1145 may push the leaflet material 1115 in toward the delivery system (similar to delivery system 310 in FIG. 3, or the like), away from the frame 1120.

Figure 12A:
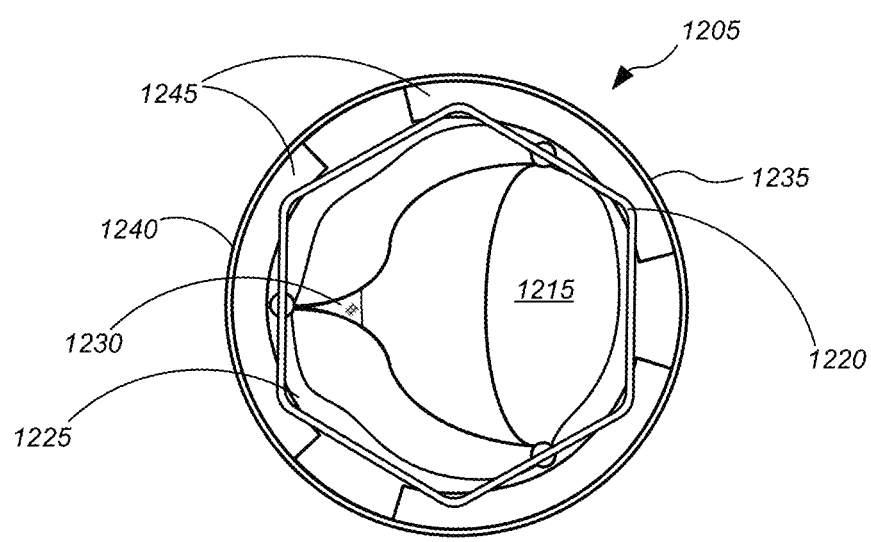
FIGS. 12A and 12B are diagrams illustrating various non-limiting examples of an implant tissue protection tool that may be used to protect at least one tissue layer of a medical device through two or more outflow cells of the medical device during crimping of the medical device prior to implantation of the medical device within a body of a subject, in accordance with various embodiments.
Figure 12B:
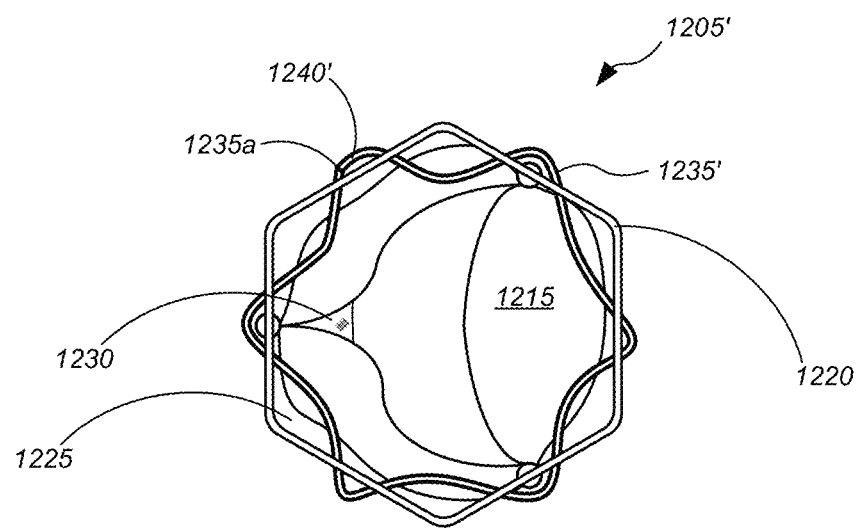

FIGS. 12A and 12B (collectively, "FIG. 12") are diagrams illustrating various non-limiting examples 1200 and 1200' of an implant tissue protection tool that may be used to protect at least one tissue layer of a medical device through two or more outflow cells of the medical device during crimping of the medical device prior to implantation of the medical device within a body of a subject, in accordance with various embodiments. FIGS. 12A and 12B depict a medical device 1205 that is similar to any one of the medical devices 405, 505, 605, 705, 805, 905, 1005, or 1105 of FIG. 4, 5, 6, 7, 8, 9, 10, or 11, respectively. Like these above-described medical devices, medical device 1205 may comprise a frame or stent 1220 that defines a plurality of outflow cells 1225, at least one tissue layer 1215 (e.g., leaflets or leaflet structure, or the like), and an inner and/or outer skirt 1230, and/or the like.

With reference to FIG. 12A, implant tissue protection tool 1235 may comprise an outer portion 1240 and a plurality of protrusions 1245. The outer portion 1240 may be similar, if not identical, to any one of the outer portions 440, 540, 640, 740, or 940 of FIG. 4, 5, 6, 7, or 9, respectively. Each of the plurality of protrusions 1245 may be similar to any one of the protrusions 445, 545, 645, or 745 of FIG. 4, 5, 6, or 7, respectively, except that where protrusions 445, 545, 645, or 745 are aligned, configured, or oriented such that their axes (or lengths) are substantially parallel with the axis of their corresponding outer portions 440, 540, 640, or 740 (or medical devices 405, 505, 605, or 705) and are configured to fit vertically through the outflow cells, each protrusion 1245 is aligned, configured, or oriented such that its axis (or length) is substantially perpendicular to the axis of outer portion 1240 (or medical device 1205) and/or substantially parallel to a plane defined by an edge or cross-section of the outer portion 1240 (or medical device 1205). In particular, each protrusion is configured to span more than one (in some cases, two) adjacent outflow cells 1225. In some instances, each protrusion may be configured to span two adjacent outflow cells 1225 such that two adjacent leaflets 1215 (per protrusion) are pushed inward to prevent pinching (as shown in the non-limiting embodiment of FIG. 12A). Alternatively, each protrusion may be configured to span two adjacent outflow cells 1225 such that a single leaflet 1215 (per protrusion) is pushed inward to prevent pinching (not shown). In yet another alternative, each protrusion may be configured to span three or more adjacent outflow cells 1225 such that multiple leaflets 1215 (per protrusion) are pushed inward to prevent pinching (not shown). In still another alternative, a single protrusion may be configured to wrap around the first (or inner surface of the outer portion 1240 (either with its ends joined or with a gap between its ends), and to span a plurality (if not all) of adjacent outflow cells 1225 such that all leaflets 1215 are pushed inward to prevent pinching (not shown).

Referring to FIG. 12B, implant tissue protection tool 1235' may be similar to the band structure of implant tissue protection tool 935 of FIG. 9, and may comprise an outer portion 1240' and a join 1235a. Implant tissue protection tool 1235' may be weaved in and out of all adjacent outflow cells 1225 such that the portions of the outer portion 1240' that lie inward of the frame or stent 1220 are configured to push the leaflets 1215 inward to prevent pinching. To remove the implant tissue protection tool 1235' (such as after partial crimp as shown and described below with respect to FIGS. 13C and 13D below), the outer portion may be cut (either along the join 1235a or along some other portion of the outer portion). In some cases, the join 1235a may be perforated or otherwise weakened to facilitate removal of the implant tissue protection tool 1235' after partial crimp.

FIGS. 13A-13E (collectively, "FIG. 13") are diagrams illustrating a non-limiting example 1300 of a use of an implant tissue protection tool for protecting at least one tissue layer of a medical device or implant during crimping of the medical device or implant prior to implantation of the medical device within a body of a subject, in accordance with various embodiments. FIG. 13 depicts assemblies and their component medical devices and implant tissue protection tools each comprising similar components as those of the corresponding components of FIG. 4, and similar reference numerals (particularly the last two digits of the reference numerals) denote similar components. For example, medical device 405 (and components 415-430) corresponds to medical device 1305 (and components 1315-1330). Similarly, implant tissue protection tool 435 (and components 440 and 445) corresponds to implant tissue protection tool 1335 (and components 1340 and 1345). Accordingly, unless otherwise indicated below, the description of medical device 405 (and components 415-430) and implant tissue protection tool 435 (and components 440 and 445) would similarly apply to the corresponding components of medical device 1305 (and its corresponding components) and implant tissue protection tool 1335 (and its corresponding components). Alternatively, although not shown, the implant tissue protection tool of the non-limiting example of FIG. 13 may be embodied by any of the implant tissue protections tools as shown and described above with respect to FIGS. 5-12.

Figure 13A:
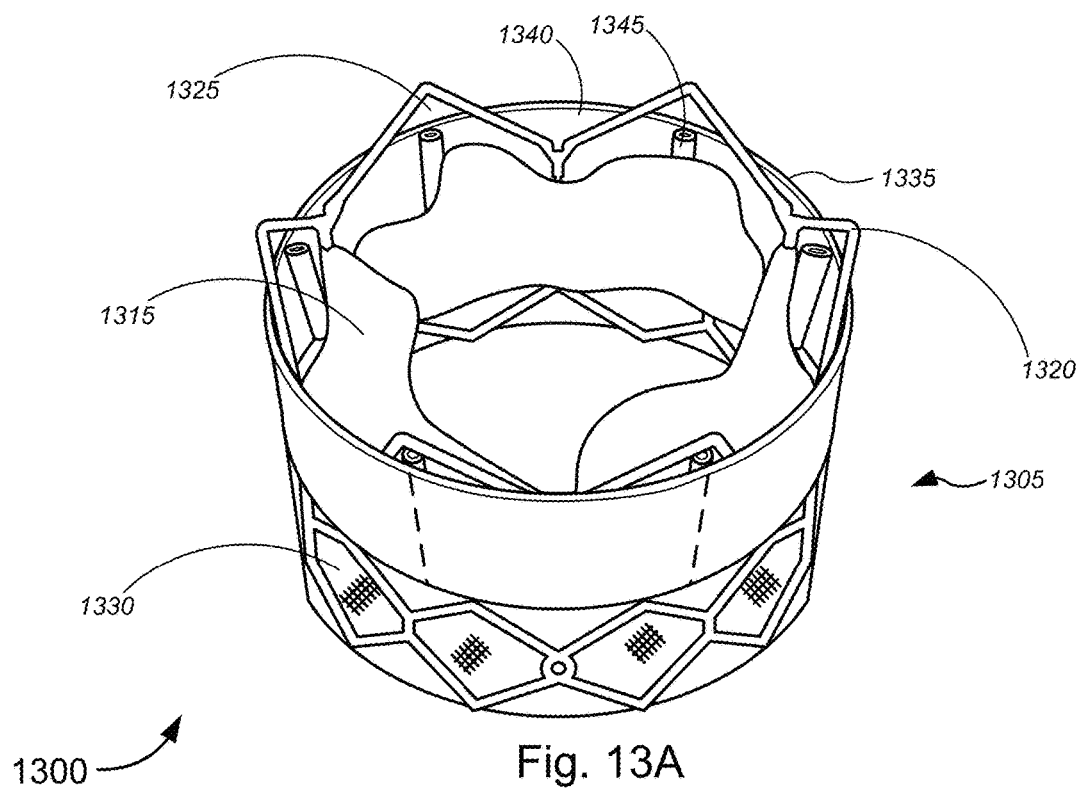
FIGS. 13A-13E are diagrams illustrating a non-limiting example of a use of an implant tissue protection tool for protecting at least one tissue layer of a medical device or implant during crimping of the medical device or implant prior to implantation of the medical device within a body of a subject, in accordance with various embodiments.
Figure 13B:
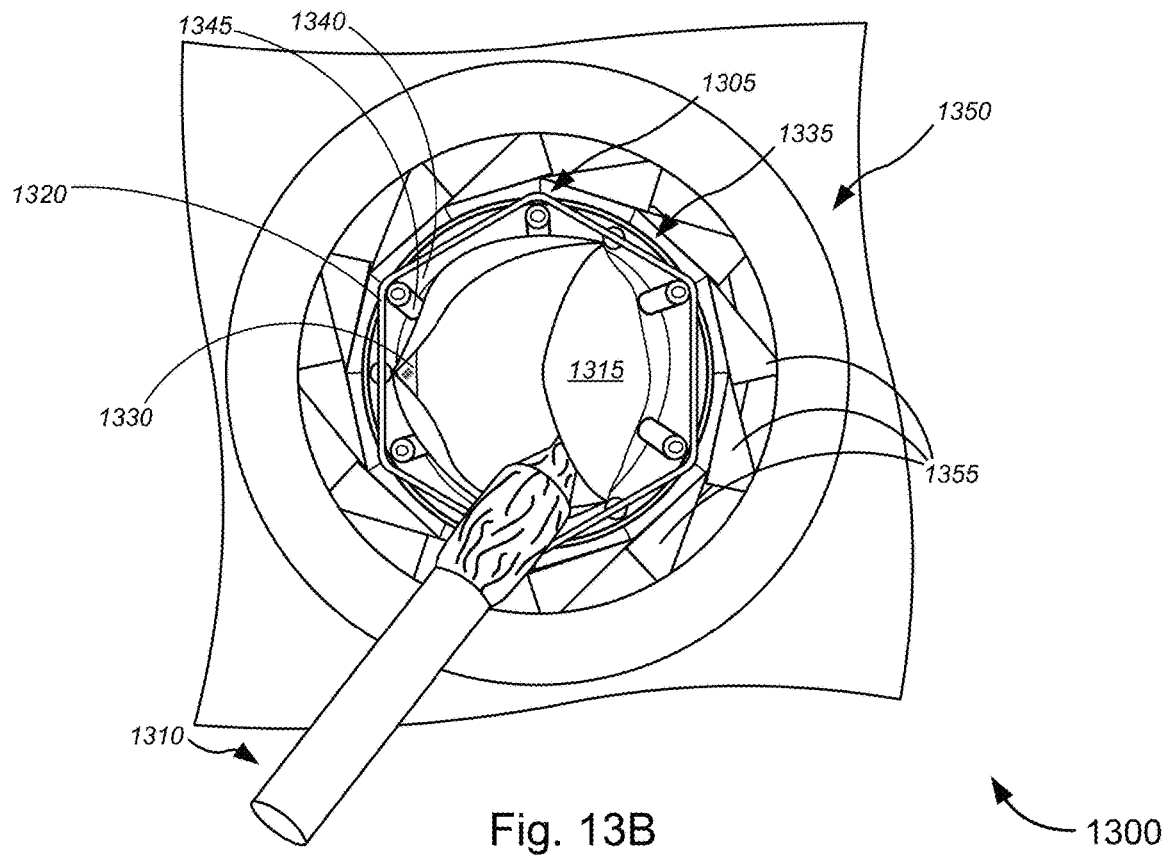
Figure 13C:
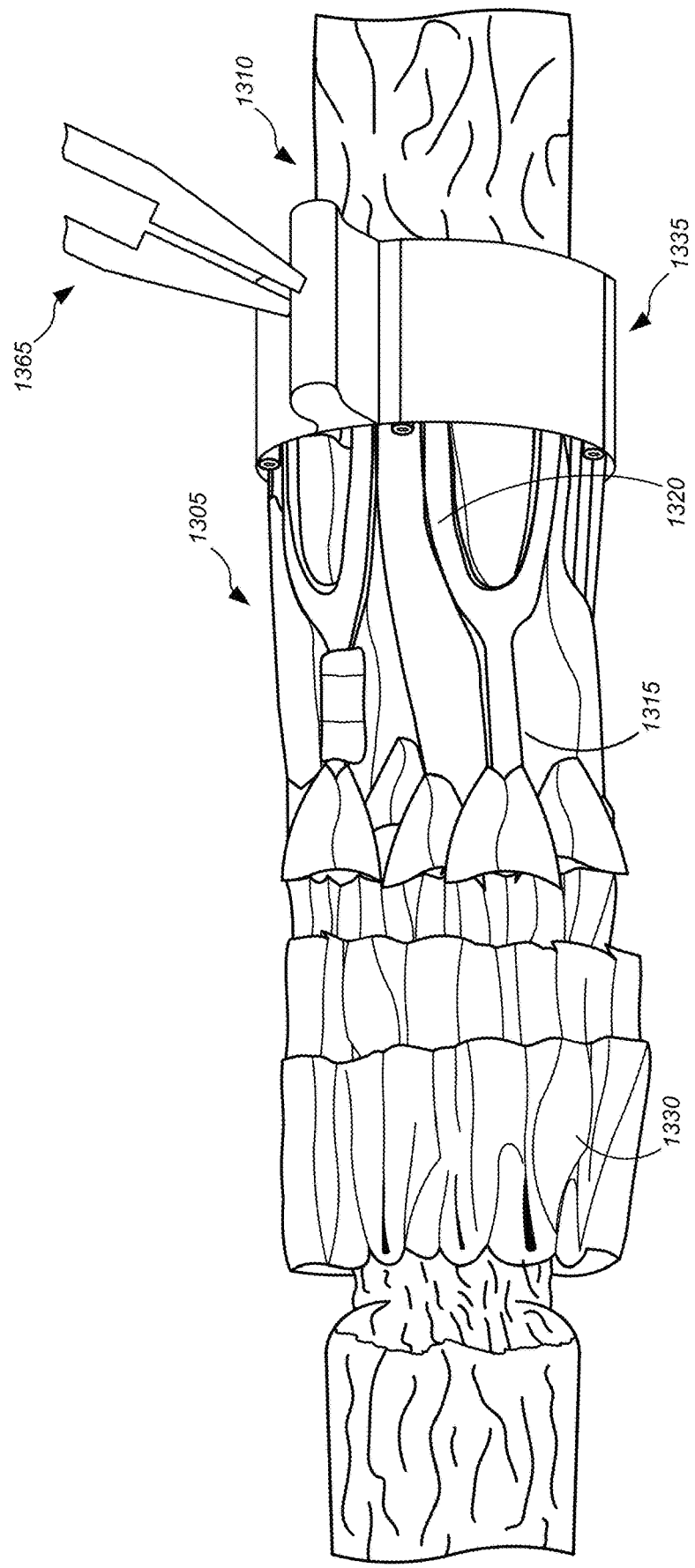
Figure 13D:
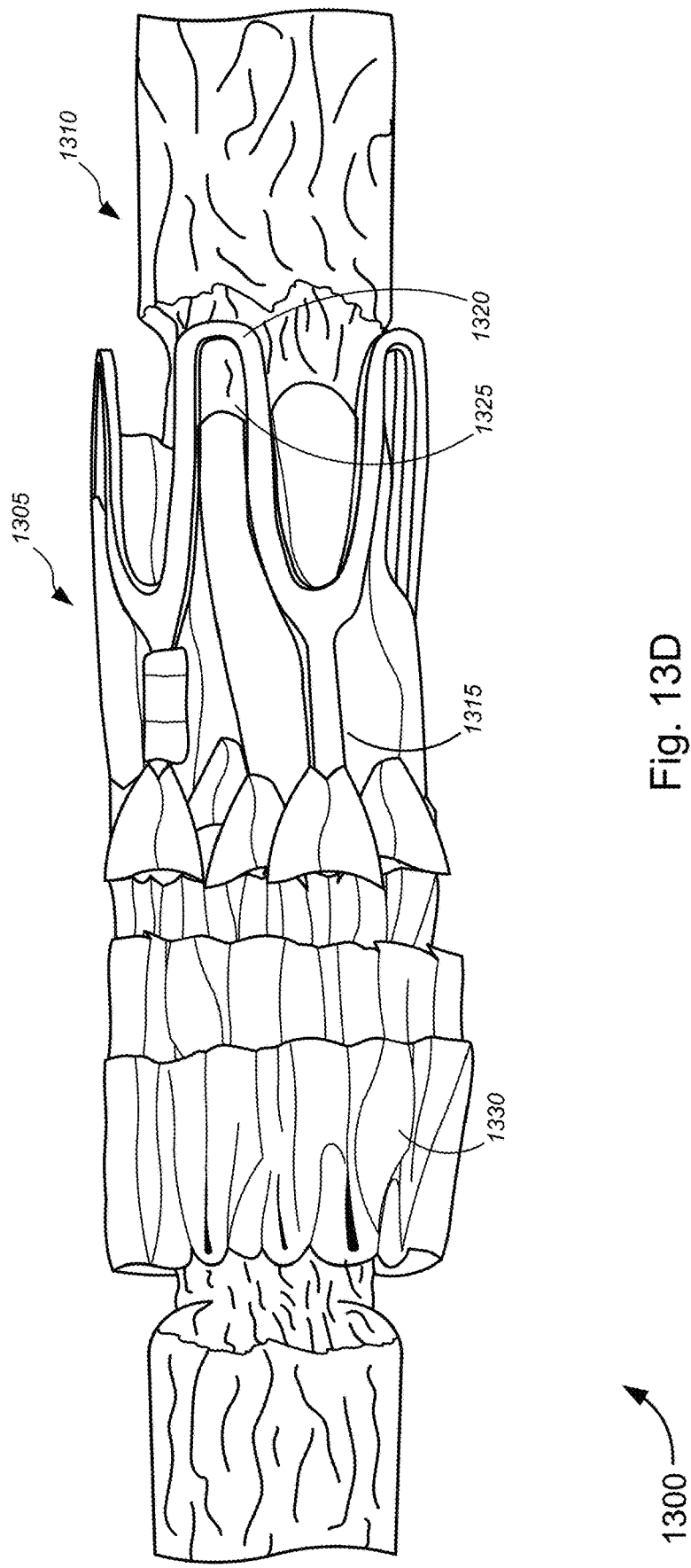
Figure 13E:
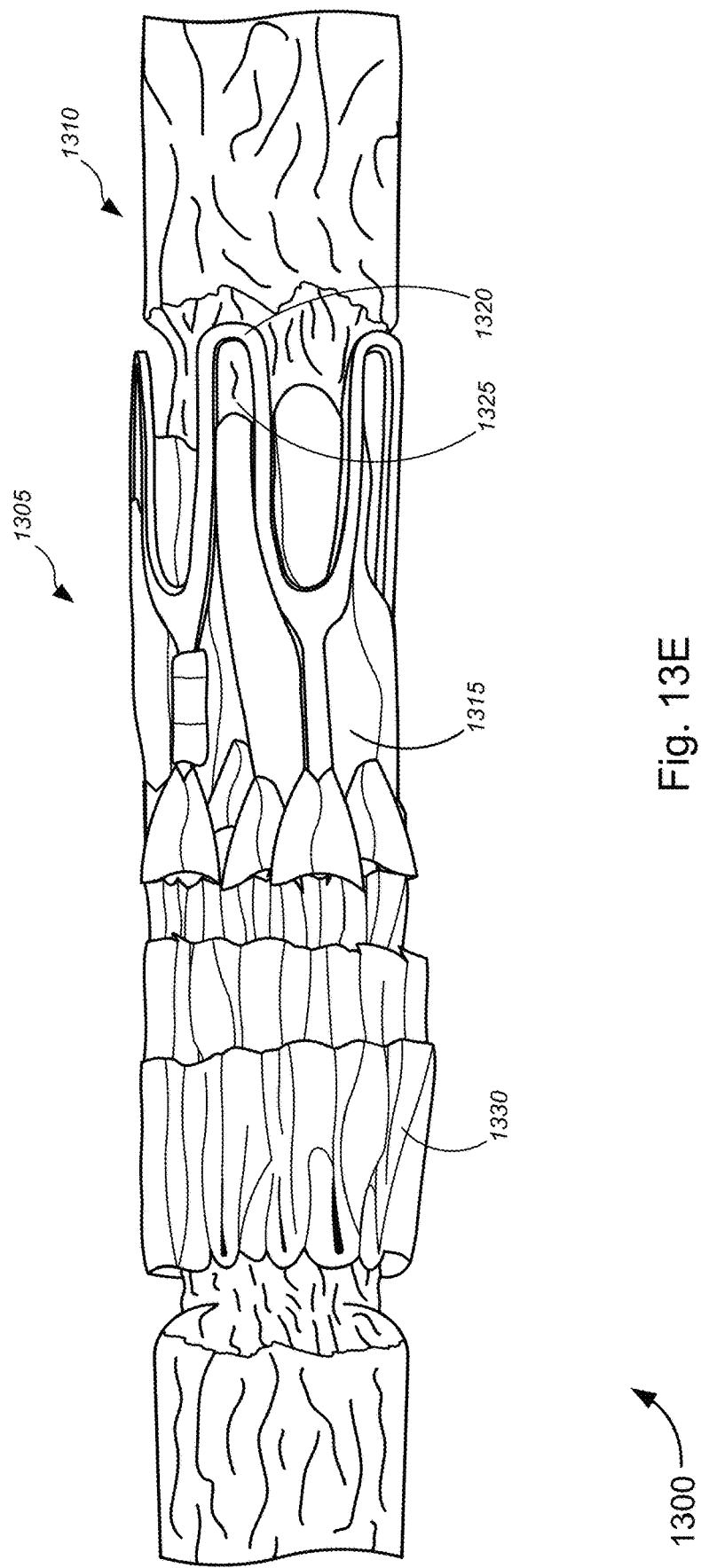

Referring to the non-limiting example 1300 of FIG. 13A, implant tissue protection tool 1335 (if not already affixed) is first removably affixed to medical device 1305. An assembly is then formed by inserting a delivery system 1310 (similar to delivery system 310 of FIG. 3, or the like) axially through the middle portion of the medical device 1305 having the implant tissue protection tool removably affixed thereto. As shown in, e.g., FIG. 13B, the assembly is inserted into a crimping device 1350 having a plurality of crimping jaws 1355. Alternatively, the medical device 1305 having the implant tissue protection tool removably affixed thereto may be inserted into the crimping device 1350, prior to the delivery system 1310 being inserted axially through the middle portion of the medical device 1305. Although a particular crimping device is shown in FIG. 13, the various embodiments are not so limited, and any suitable crimping device may be used, including, but not limited to, an automated crimping device, a mechanical-assist crimping device, a manual crimping device, or a tapered capsule-based passive crimping device, and/or the like.

A partial crimp of the assembly is performed, using the crimping device 1350, to reduce a first diameter of the assembly to a second diameter smaller than the first diameter, wherein, during the partial crimp, the at least one protrusion actively pushes radially inward on the at least one tissue layer, thereby minimizing occurrence of the at least one tissue layer of the medical device passing through at least one opening defined at least in part by two or more struts of the medical device during crimping of the medical device. The implant tissue protection tool 1335 may then be removed (as shown, e.g., in FIG. 13C, or the like), in some cases, with use of forceps 1365 or other suitable tools. As shown, e.g., in FIG. 13D, the partially crimped medical device 1305 is positioned about a narrow portion of the delivery system 1310. If necessary, a position of the medical device 1305 may be adjusted on (or relative to) the delivery system 1310. A final crimp of the assembly (without the implant tissue protection tool 1335) may be performed using the crimping device 1350 (of FIG. 13B), to reduce the second diameter of the assembly to a third diameter smaller than the second diameter (as shown, e.g., in FIG. 13E, or the like), in preparation for implantation of the medical device 1305 into the body of the subject.

FIGS. 14A-14I (collectively, "FIG. 14") are diagrams illustrating various non-limiting examples 1400, 1400', 1400", 1400''', 1400"", and 1400''''' of an implant tissue protection tool, including at least one separation device, that may be used to protect at least one tissue layer of a medical device during crimping of the medical device prior to implantation of the medical device within a body of a subject, in accordance with various embodiments. FIG. 14 depicts assemblies and their component medical devices and implant tissue protection tools each comprising similar components as those of the corresponding components of at least one of FIG. 4, and similar reference numerals (particularly the last two digits of the reference numerals) denote similar components. For example, medical device 405 (and components 415-430) corresponds to medical device 1405 (and components 1415-1430). Similarly, implant tissue protection tool 435 (and components 440 and 445) corresponds to implant tissue protection tool 1435 (and components 1440 and 1445). Accordingly, unless otherwise indicated below, the description of medical device 405 (and components 415-430) and implant tissue protection tool 435 (and components 440 and 445) would similarly apply to the corresponding components of medical device 1405 (and its corresponding components) and implant tissue protection tool 1435 (and its corresponding components). Alternatively, although not shown, the implant tissue protection tool of the non-limiting example of FIG. 14 may be embodied by any of the implant tissue protections tools similar to those as shown and described above with respect to FIGS. 5-12.

With reference to FIG. 14, a medical device 1405, which might include, without limitation, at least one tissue layer 1415 (in this case, a prosthetic valve similar to prosthetic valve 142 of FIG. 1, or the like, which may include one or more leaflets or leaflet structures, or the like) and a stent or frame 1420 (similar to stent 102 of FIG. 1, or the like, which may include a plurality of struts, a plurality of crowns, and/or a plurality of axial frame members, and/or the like). The stent or frame 1420 may include a plurality of openings or cells that are defined at least in part by two or more struts among the plurality of struts (and, in some cases, also by one or more crowns among the plurality of crowns and/or by one or more axial frame members among the plurality of axial frame members, and/or the like). In some instances, the stent or frame 1420 may further include an inflow portion (similar to inflow portion 108 of FIG. 1, or the like) and an outflow portion (similar to the combination of outflow portion 118 and transition portion 124 of FIG. 1, or the like), with the inflow portion being substantially covered by at least an outer skirt 1430 (and, in some cases, also by an inner skirt (not shown in FIG. 14) or an inner skirt instead of an outer skirt (also not shown in FIG. 14)). Outflow openings 1425, which are not covered by a skirt (whether outer or inner skirt), may present a pinch risk during crimping of the medical device 1405 for delivery to an implantation site (e.g., a native heart valve, or other suitable implantation site, or the like) in a body of a subject, due to its design, particularly if the outflow openings 1425 defined at least in part by the two or more struts (and, in some cases, the one or more crowns and/or the one or more axial frame members, and/or the like) in the outflow portion of the stent or frame 1420 is substantially larger than the inflow openings defined by corresponding struts (and, in some cases, crowns) in the inflow portion of the stent or frame 1420.

The implant tissue protection tool 1435 may include, but is not limited to, an outer portion 1440, at least one protrusion 1445 affixed to a first surface of the outer portion 1440 (in some cases, integrally formed from the outer portion, or the like), and at least one separation or removal device 1460 affixed to the outer portion 1440. The outer portion 1440 may be configured to surround one or more outer segments of the at least one tissue layer 1415 of the medical device 1405 to be implanted into the body of the subject. The at least one protrusion 1445 may be configured to minimize (and, in some cases, prevent) occurrence (or likelihood of occurrence) of the at least one tissue layer 1415 of the medical device 1405 passing through at least one opening 1425 defined during crimping of the medical device 1405 by a crimping device (such as shown in FIG. 13B, or the like) in preparation for implantation into the body of the subject. That is, the at least one protrusion 1445 may be configured to actively push radially inward against the at least one tissue layer 1415 of the medical device 1405 to minimize (and, in some cases, prevent) pinching of the at least one tissue layer 1415 by two or more struts (or other stent or frame structure) 1420 of the medical device 1405 while the medical device 1405 is being crimped in preparation for delivery of the medical device 1405 to an implantation site within the body of the subject. The at least one separation or removal device 1460 may be configured to facilitate efficient separation or removal of the implant tissue protection tool 1435 from the medical device 1405 and to facilitate preferential orientation or folding direction of the at least one tissue layer of the medical device and/or components of the medical device 1405. The implant tissue protection tool 1435 described herein is separate from, and has a structure as a whole that is independent of, the crimping device. Although a particular crimping device is described with respect to FIG. 14, the various embodiments are not so limited, and any suitable crimping device may be used, including, but not limited to, an automated crimping device, a mechanical-assist crimping device, a manual crimping device, or a tapered capsule-based passive crimping device, and/or the like.

In some embodiments, the implant tissue protection tool 1435 may be embodied by any of the configurations shown and described above with respect to FIGS. 4-12. According to some embodiments, the at least one separation device comprises a plurality of separation devices 1460 that is affixed to and arranged at intervals around an outer perimeter of the outer portion 1440. In some instances, the plurality of separation devices 1460 may include at least three separation devices 1460 that are spaced substantially equidistant around the outer perimeter of the outer portion 1440 (such as shown, e.g., in the non-limiting embodiments of FIGS. 14A and 14C-14F, or the like). In some cases, the at least one separation device 1460 may have a form type or shape including, but not limited to, one of a side loop configuration 1460a (such as shown, e.g., in non-limiting embodiment 1400 of FIG. 14A, or the like), a bunny ear configuration 1460b (such as shown, e.g., in non-limiting embodiment 1400' of FIG. 14B, or the like), a tab or upper tab configuration 1460c (such as shown, e.g., in non-limiting embodiment 1400'' of FIGS. 14C and 14D, or the like), a basket handle configuration 1460d (such as shown, e.g., in non-limiting embodiment 1400''' of FIGS. 14E-14G, or the like), or a suture loop configuration 1460e (such as shown, e.g., in non-limiting embodiment 1400'''' of FIG. 14H, or the like), and/or the like. Alternatively, or additionally, the at least one separation device 1460 may have a general form type or shape comprising one of a loop configuration or a tab configuration, or the like. The loop configuration (which may include, without limitation, the side loop configuration, a basket handle configuration, or a suture loop configuration, etc.) may comprise a center area without any material and may be bound at the edges. The tab configuration (which may include, but is not limited to, the bunny ear configuration, the upper tab configuration, etc.) may be without a center opening. In some cases, the shape of the at least one separation device 1460 may comprise any suitable shape including, without limitation, polygonal, circular, elliptical, and/or the like. Alternatively, the implant tissue protection tool 1435 may be made of a material that is capable of being perforated and torn, where the outer portion 1440 may include a perforation 1460f along an entire longitudinal length thereof (such as shown, e.g., in non-limiting embodiment 1400' of FIG. 14I, or the like), or the like.

We now turn to the specific, non-limiting examples shown in FIGS. 14A-14I. In each of the non-limiting examples shown in FIGS. 14A-14I, the at least one (or the plurality of) separation or removal devices 1460 each provides a structure that enables a user to grab with fingers or a tool (e.g., forceps, pliers, or the like) in order to separate, remove, or otherwise free the implant tissue protection tool 1435 from a medical device 1405 to which it may be removably affixed (such as shown in FIGS. 4A and 13A, or the like). Separation or removal of the implant tissue protection tool 1435 from the medical device 1405 would occur after partial crimping and before final crimping of the medical device 1405, in a manner as described above with respect to FIG. 13, or the like.

Figure 14A:
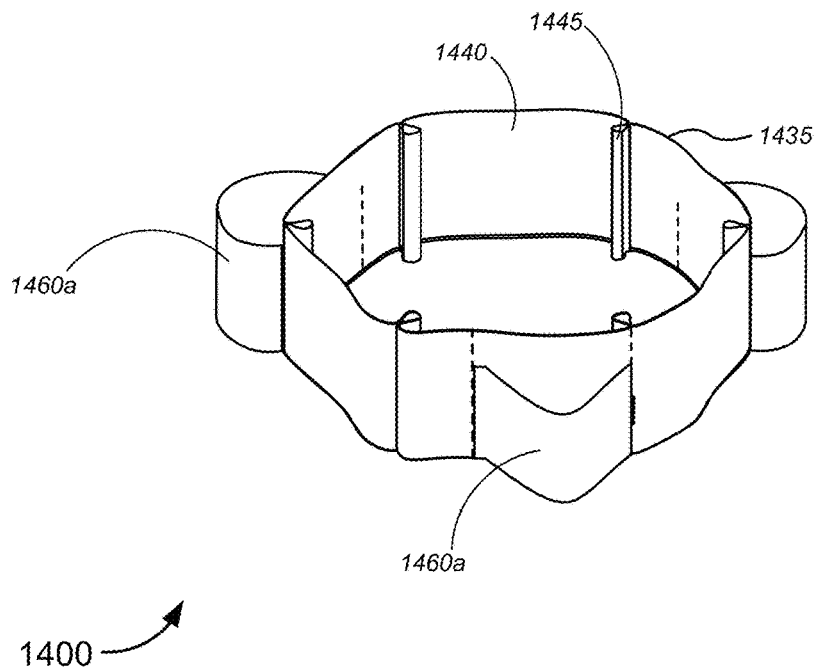

FIG. 14A depicts a non-limiting example 1400 of an implant tissue protection tool 1435 (similar to that as shown and described above with respect to FIGS. 4 and 13) that includes an outer portion 1440, a plurality of protrusions 1445, and a plurality of (in this case, three) separation or removal devices 1460a that each has a form or shape of a side loop configuration, in which a loop of material is affixed (e.g., by stitches or sutures, or the like) to a second (outer) surface of the outer portion 1440 that is opposite from the first (inner) surface on which the protrusions 1445 are disposed. In other words, the separation or removal devices 1460a are disposed on the sides of the implant tissue protection tool 1435. In some instances, the side loops or separation devices 1460a may be arranged at intervals (in some cases, in substantially equidistant positions, or the like) along the outer perimeter of the outer portion 1440. In this manner, regardless of which side of the implant tissue protection tool 1435 a user might be closest to or might be able to view, the user will have access to at least one of the side loops or separation devices 1460a for grabbing onto with finger or tool to aid in removal of the implant tissue protection tool 1435 from the medical device to which it may be removably affixed, during the crimping process as described above with respect to FIG. 13. Although not shown, the side loops or separation devices 1460a may be arranged in a non-equidistant manner along the outer perimeter of the outer portion 1440. In some cases, any number of side loops or separation devices 1460a (with at least one side loop) may be used.

Figure 14B:
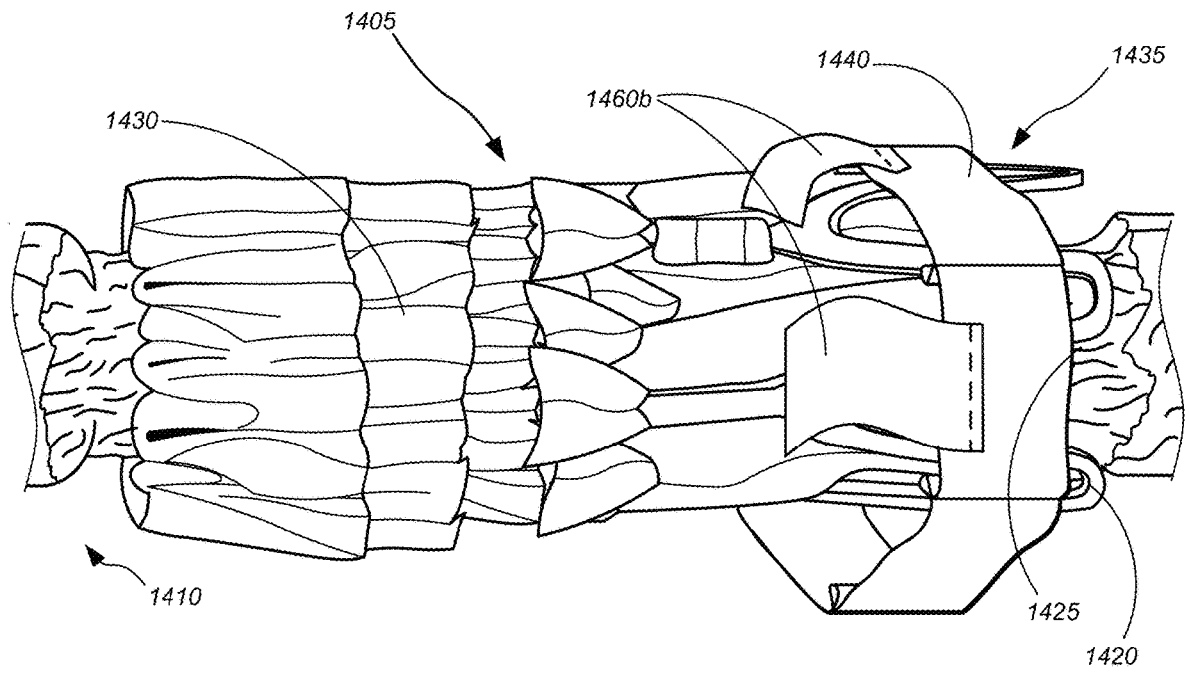

FIG. 14B depicts a non-limiting example 1400' of an implant tissue protection tool 1435 (similar to that as shown and described above with respect to FIGS. 4 and 13) that includes an outer portion 1440, a plurality of protrusions 1445, and a plurality of (in this case, three) separation or removal devices 1460b that each has a form or shape of a bunny ear configuration, in which a flap of material is affixed (e.g., by stitches or sutures, or the like) to a second (outer) surface of the outer portion 1440 that is opposite from the first (inner) surface on which the protrusions 1445 are disposed. In other words, the separation or removal devices 1460b are disposed on the sides of the implant tissue protection tool 1435. In some instances, the bunny ears or separation devices 1460b may be arranged at intervals (in some cases, in substantially equidistant positions, or the like) along the outer perimeter of the outer portion 1440. In this manner, regardless of which side of the implant tissue protection tool 1435 a user might be closest to or might be able to view, the user will have access to at least one of the bunny ears or separation devices 1460b for grabbing onto with finger or tool to aid in removal of the implant tissue protection tool 1435 from the medical device to which it may be removably affixed, during the crimping process as described above with respect to FIG. 13. The bunny ears or separation devices 1460b may either include or lack tack stitches for identification purposes. Although not shown, the bunny ears or separation devices 1460b may be arranged in a non-equidistant manner along the outer perimeter of the outer portion 1440. In some cases, any number of bunny ears or separation devices 1460b (with at least one bunny ear) may be used.

Figure 14C:
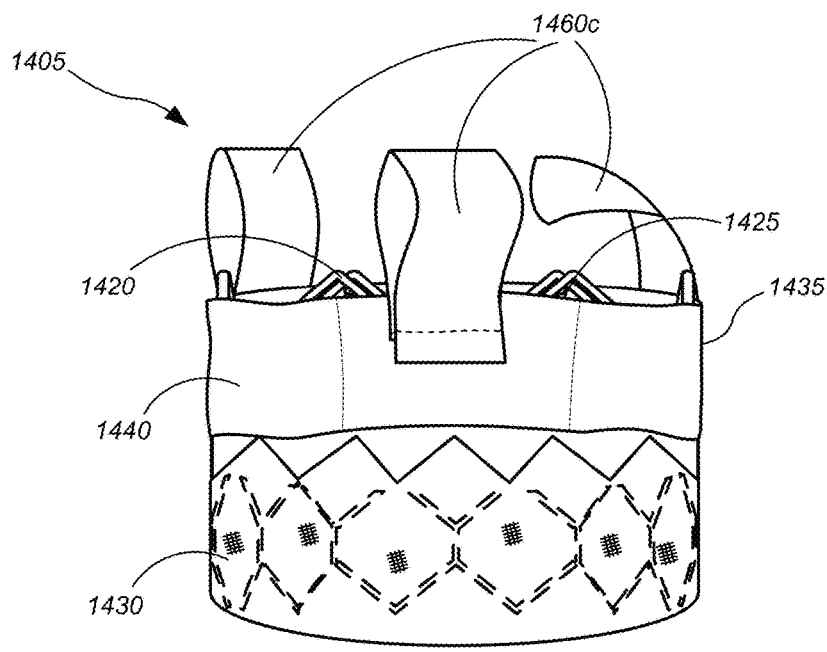
Figure 14D:
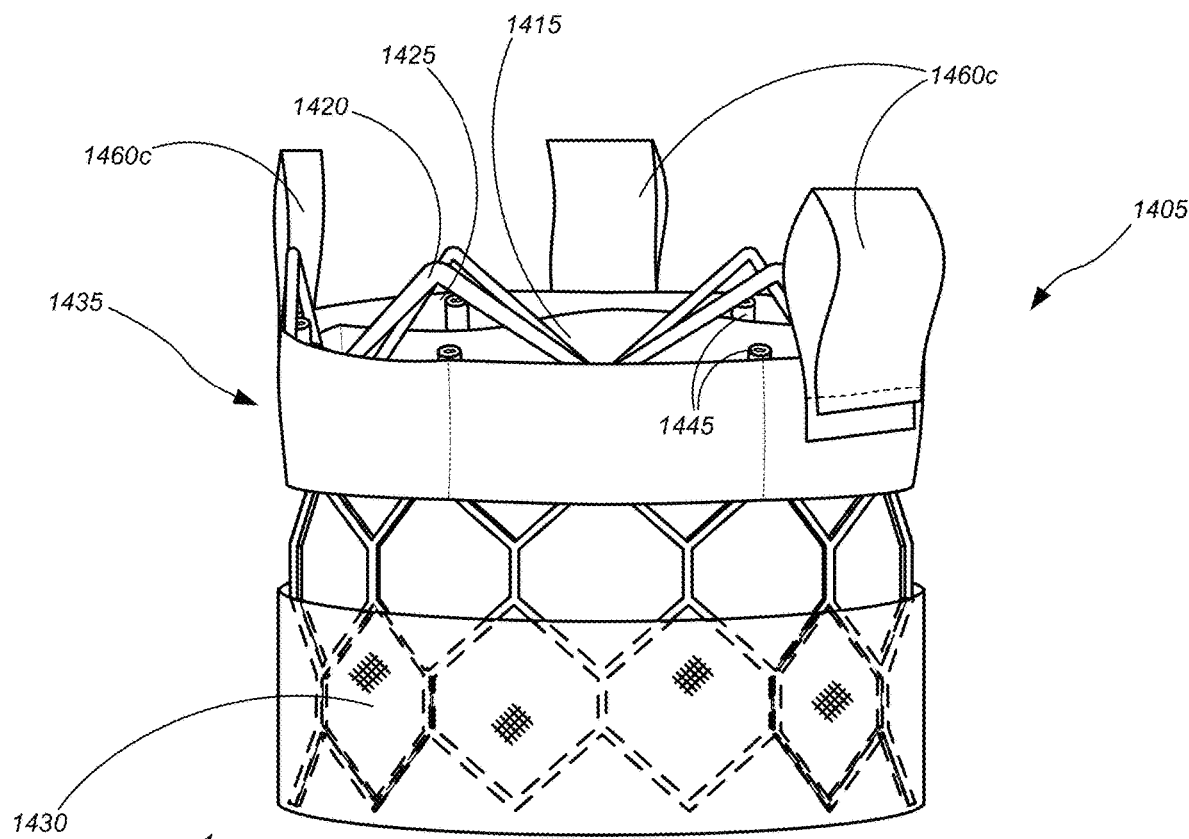

FIGS. 14C and 14D depict a non-limiting example 1400'' of an implant tissue protection tool 1435 (similar to that as shown and described above with respect to FIGS. 4 and 13) that includes an outer portion 1440, a plurality of protrusions 1445, and a plurality of (in this case, three) separation or removal devices 1460c that each has a form or shape of a tab or upper tab configuration, in which a folded over flap of material is affixed (e.g., by stitches or sutures, or the like) to a second (outer) surface of the outer portion 1440 that is opposite from the first (inner) surface on which the protrusions 1445 are disposed, the folded over flap extending beyond the longitudinal length of the outer portion or of the implant tissue protection tool 1435. In other words, the separation or removal devices 1460c are disposed on the sides of the implant tissue protection tool 1435, while extending beyond a top portion thereof (as shown, e.g., in FIGS. 14C and 14D, or the like). In some instances, the tabs or separation devices 1460c may be arranged at intervals (in some cases, in substantially equidistant positions, or the like) along the outer perimeter of the outer portion 1440. In this manner, regardless of which side of the implant tissue protection tool 1435 a user might be closest to or might be able to view, the user will have access to at least one of the tabs or separation devices 1460c for grabbing onto with finger or tool to aid in removal of the implant tissue protection tool 1435 from the medical device to which it may be removably affixed, during the crimping process as described above with respect to FIG. 13. Although not shown, the tabs or separation devices 1460c may be arranged in a non-equidistant manner along the outer perimeter of the outer portion 1440. In some cases, any number of tabs or separation devices 1460c (with at least one tab) may be used. The tabs or separation devices 1460c extending beyond the top portion (or proximal or outflow end) of the implant tissue protection tool 1435 allows pulling of the implant tissue protection tool towards the proximal or outflow end to avoid (or at least minimize occurrence of) inverting of the at least one tissue layers 1415 (e.g., leaflets in the case that the medical device 1405 is a prosthetic valve, or the like). The tabs or separation devices 1460c may be of varying lengths. For example, lengths between 12-20 mm are designed to be sufficiently long for users to grab with fingertips, but are not overly long to become a nuisance during handling.

Figures 14E, 14F:
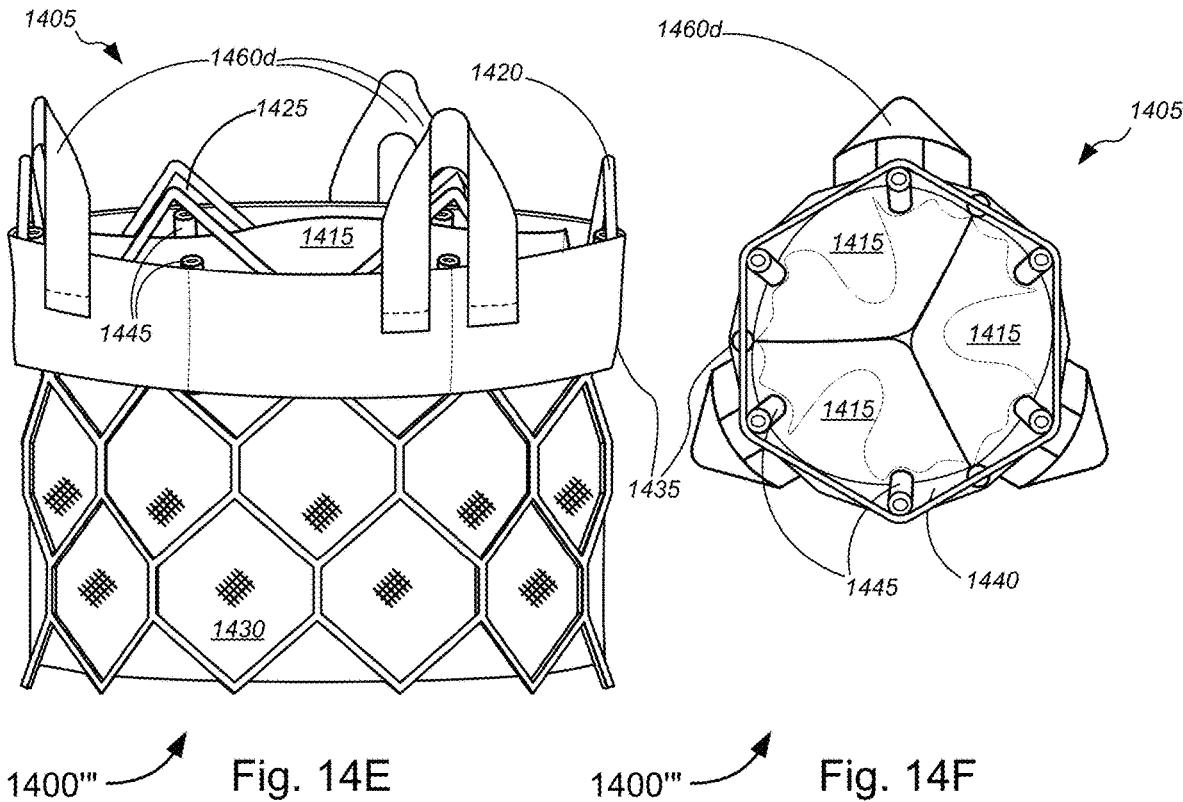
Figure 14G:
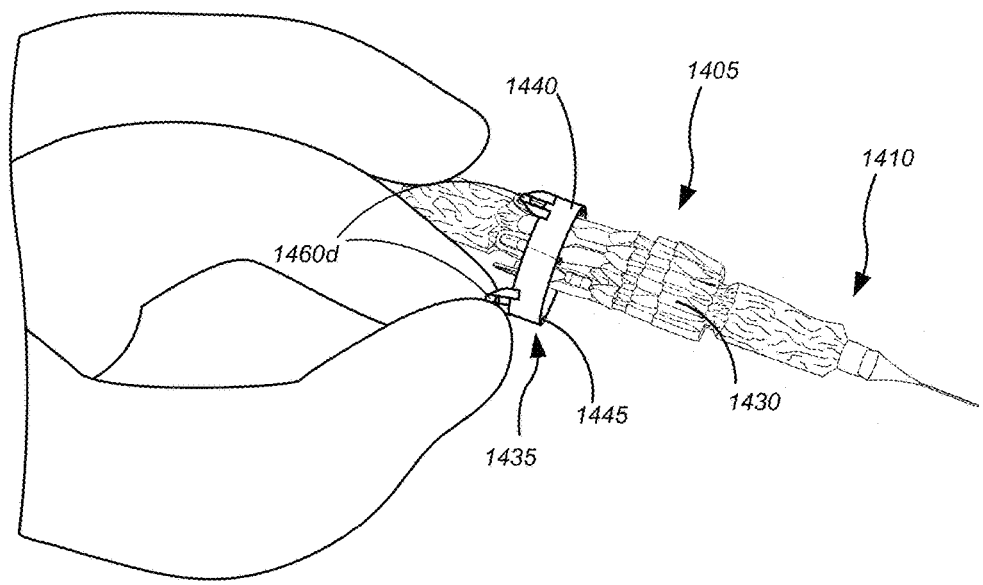

FIGS. 14E-14G depict a non-limiting example 1400''' of an implant tissue protection tool 1435 (similar to that as shown and described above with respect to FIGS. 4 and 13) that includes an outer portion 1440, a plurality of protrusions 1445, and a plurality of (in this case, three) separation or removal devices 1460d that each has a form or shape of a basket handle configuration, in which a bent strip of material is affixed (e.g., by stitches or sutures, or the like) to two portions of a second (outer) surface of the outer portion 1440 that is opposite from the first (inner) surface on which the protrusions 1445 are disposed, the bent strips extending beyond the longitudinal length of the outer portion or of the implant tissue protection tool 1435. In other words, the separation or removal devices 1460d are disposed on the sides of the implant tissue protection tool 1435, while extending beyond a top portion thereof (as shown, e.g., in FIGS. 14E and 14G, or the like). In some instances, the basket handles or separation devices 1460d may be arranged at intervals (in some cases, in substantially equidistant positions, or the like) along the outer perimeter of the outer portion 1440. In this manner, regardless of which side of the implant tissue protection tool 1435 a user might be closest to or might be able to view, the user will have access to at least one of the basket handles or separation devices 1460d for grabbing onto with finger or tool to aid in removal of the implant tissue protection tool 1435 from the medical device to which it may be removably affixed, during the crimping process as described above with respect to FIG. 13. Although not shown, the basket handles or separation devices 1460d may be arranged in a non-equidistant manner along the outer perimeter of the outer portion 1440. In some cases, any number of basket handles or separation devices 1460a (with at least one basket handle) may be used. The basket handles or separation devices 1460d extending beyond the top portion (or proximal or outflow end) of the implant tissue protection tool 1435 allows pulling of the implant tissue protection tool towards the proximal or outflow end to avoid (or at least minimize occurrence of) inverting of the at least one tissue layers 1415 (e.g., leaflets in the case that the medical device 1405 is a prosthetic valve, or the like). The basket handles or separation devices 1460d may be of varying lengths. For example, lengths between 12-20 mm are designed to be sufficiently long for users to grab with fingertips, but are not overly long to become a nuisance during handling.

FIG. 14H depicts a non-limiting example 1400'''' of an implant tissue protection tool 1435 (similar to that as shown and described above with respect to FIGS. 4 and 13) that includes an outer portion 1440, a plurality of protrusions 1445, and a plurality of (in this case, three) separation or removal devices 1460e that each has a form or shape of a suture loop configuration, in which a suture is affixed (e.g., by stitches or sutures, or the like) to a second (outer) surface of the outer portion 1440 that is opposite from the first (inner) surface on which the protrusions 1445 are disposed, with the suture forming a loose loop that is extendable beyond the side or second (outer) surface of the outer portion 1440. In other words, the separation or removal devices 1460e are disposed on the sides of the implant tissue protection tool 1435. In some cases, the suture may be made of any suitable material that allows for pulling or tugging without breaking. In some instances, the suture loops or separation devices 1460e may be arranged at intervals (in some cases, in substantially equidistant positions, or the like) along the outer perimeter of the outer portion 1440. In this manner, regardless of which side of the implant tissue protection tool 1435 a user might be closest to or might be able to view, the user will have access to at least one of the suture loops or separation devices 1460e for grabbing onto with finger or tool to aid in removal of the implant tissue protection tool 1435 from the medical device to which it may be removably affixed, during the crimping process as described above with respect to FIG. 13. Although not shown, the suture loops or separation devices 1460e may be arranged in a non-equidistant manner along the outer perimeter of the outer portion 1440. In some cases, any number of suture loops or separation devices 1460e (with at least one suture loop) may be used. The suture loops or separation devices 1460e are configured to be loose to allow a user to grab onto the suture loop structure to release the implant tissue protection tool 1435 from the crimped (or partially crimped) medical device 1405.

Figure 14I:
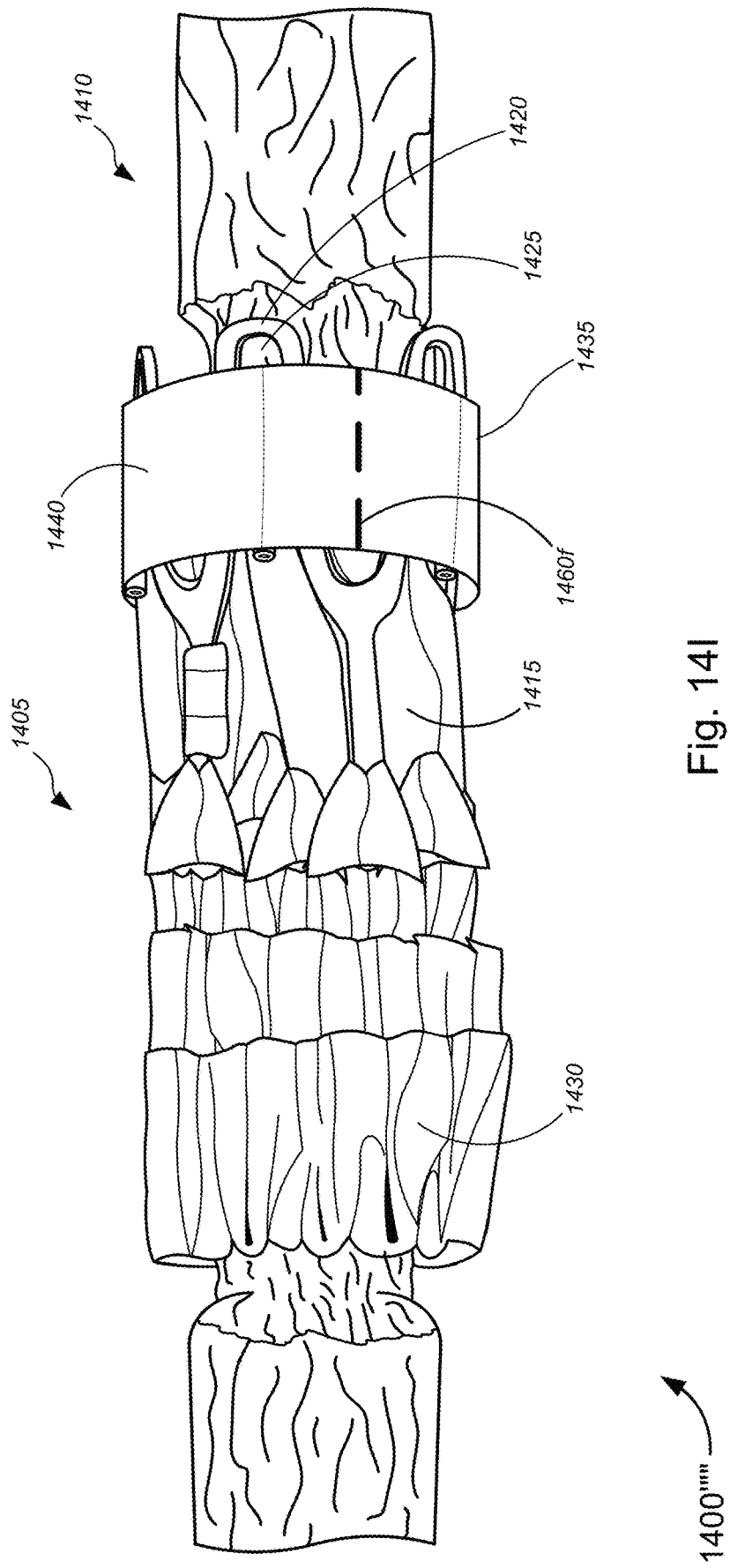

FIG. 14I depicts a non-limiting example 1400'''' of an implant tissue protection tool 1435 (similar to that as shown and described above with respect to FIGS. 4 and 13) that includes an outer portion 1440, a plurality of protrusions 1445, and at least one separation or removal device 1460f that each has a form or structure of a perforation along a longitudinal length of the outer portion 1440. In such embodiments, the implant tissue protection tool 1435 may be made of a material that is capable of being perforated and torn, where such material may include, but is not limited to, fabric or expanded polytetrafluoroethylene ("ePTFE"), or the like. In some instances, the perforations or separation devices 1460f may be arranged at intervals (in some cases, in substantially equidistant positions, or the like) along the outer perimeter of the outer portion 1440. In this manner, regardless of which side of the implant tissue protection tool 1435 a user might be closest to or might be able to view, the user will have access to at least one of the perforations or separation devices 1460f for tearing the outer portion 1440 with fingers or tools to aid in removal of the implant tissue protection tool 1435 from the medical device to which it may be removably affixed, during the crimping process as described above with respect to FIG. 13. Although not shown, the perforations or separation devices 1460f may be arranged in a non-equidistant manner along the outer perimeter of the outer portion 1440. In some cases, any number of perforations or separation devices 1460a (with at least one perforation) may be used. The perforations or separation devices 1460f may configured such that separation or removal of the implant tissue protection tool 1435 is torn away on the proximal (or outflow) side of the medical device 1405, thereby avoiding or at least minimizing occurrence of the freed implant tissue protection tool 1435 being caught on the crimped medical device 1405 when sliding the implant tissue protection tool off of the delivery system 1410.

Figure 15A:
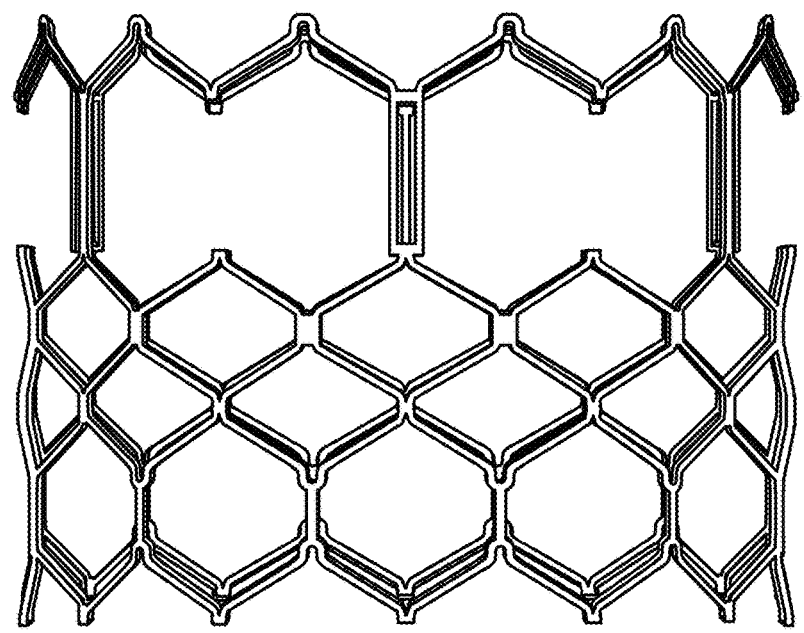
FIGS. 15A and 15B are diagrams illustrating a non-limiting example of a use of an implant tissue protection tool for protecting at least one tissue layer of another type of configuration of medical device or implant during crimping of the medical device or implant prior to implantation of the medical device within a body of a subject, in accordance with various embodiments.
Figure 15B:
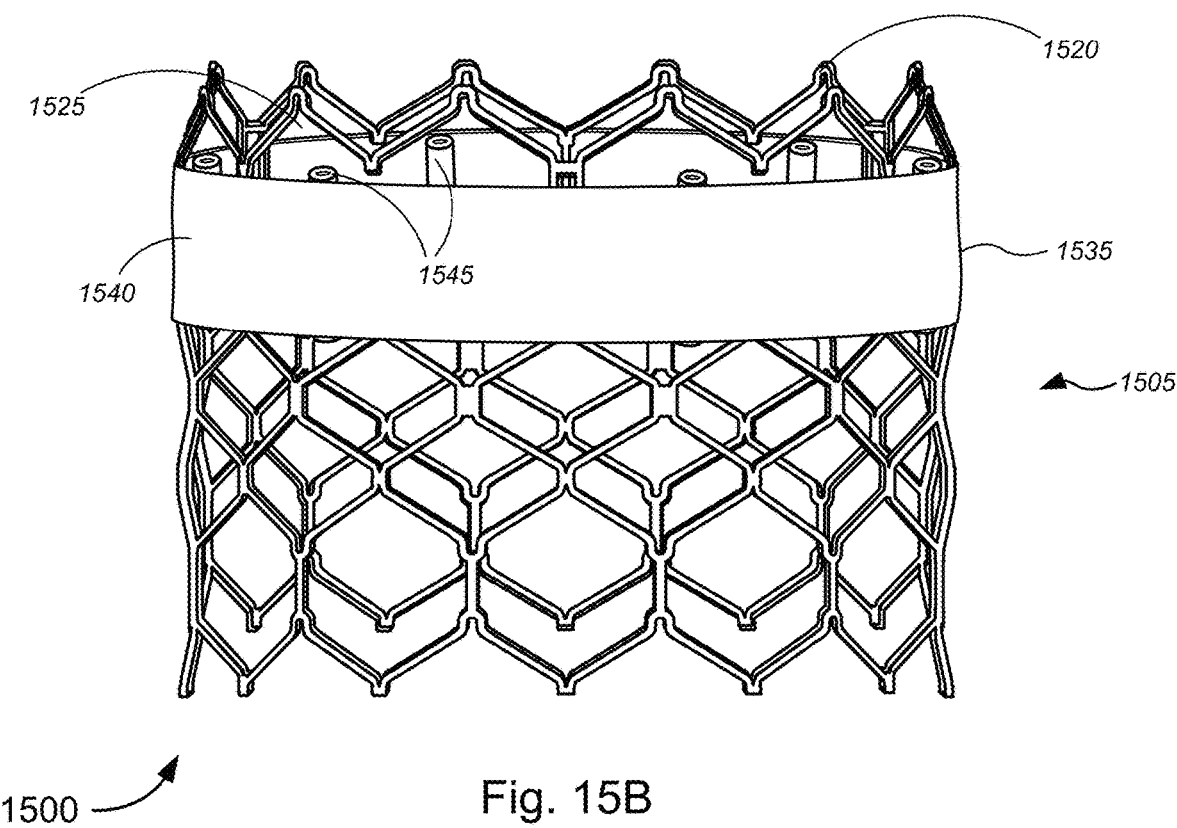

FIGS. 15A and 15B (collectively, "FIG. 15") are diagrams illustrating a non-limiting example 1500 of a use of an implant tissue protection tool 1535 for protecting at least one tissue layer of another type of configuration of medical device or implant 1505 during crimping of the medical device or implant prior to implantation of the medical device within a body of a subject, in accordance with various embodiments. FIG. 15A depicts the medical device or implant 1505 without the implant tissue protection tool 1535, while FIG. 15B depicts the medical device or implant 1505 with the implant tissue protection tool 1535 being used. As illustrated in FIG. 15, the medical device or implant 1505 comprises a frame or stent 1520 that defines a plurality of outflow cells 1525 (as well as a plurality of inflow cells below the outflow cells). As best shown in FIG. 15A, each outflow cell 1525 may have a general shape of two adjoined hexagonal cells with the vertical connecting wall removed. As depicted in FIG. 15B, the implant tissue protection tool 1535 (similar to implant tissue protection tool 435 of FIG. 4, although any one of implant tissue protection tools 435, 535, 635, 735, 835, 935, 1035, 1135, 1235, 1235', 1335, or 1435 or FIG. 4, 5, 6, 7, 8, 9, 10, 11, 12A, 12B, 13, or 14, respectively, may be used) may comprise an outer portion 1540 and a plurality of protrusions 1545 affixed to a first surface of the outer portion 1540 (in some cases, integrally formed from the outer portion, or the like). For simplicity of illustration, FIG. 15 only depicts the frame 1520 of the medical device or implant 1505 without depicting the outer skirt or the tissue layer (or leaflets), or other components shown and described above with respect to FIGS. 1-14.

As shown in FIG. 15B, implant tissue protection tool 1535 may be used for protecting at least one tissue layer of another type of configuration of medical device or implant 1505 during crimping of the medical device or implant prior to implantation of the medical device within a body of a subject, by being configured to fit over the outflow cells 1525 of the medical device or implant 1505 such that at least one protrusion 1545 among the plurality of protrusions 1545 extends inwardly through each outflow cell 1525 or each alternating outflow cell 1525. In this manner, at least one protrusion 1545 is used to push inward one leaflet of the tissue layer (not shown). Although FIG. 15 depicts one protrusion 1545 per outflow cell 1525 (or two protrusions per leaflet), the various embodiments are not so limited, and any suitable number of protrusions may be used per outflow cell 1525 or per leaflet (e.g., two protrusions per outflow cell for a total of four protrusions per leaflet, or one protrusion per every other outflow cell for a total of one protrusion per leaflet, etc.).

The embodiment 1500 of FIG. 15 would otherwise be similar if not identical to the embodiments as shown or described above with respect to FIGS. 1-14, and description of these embodiments are similar applicable to embodiment 1500.

Figure 16:
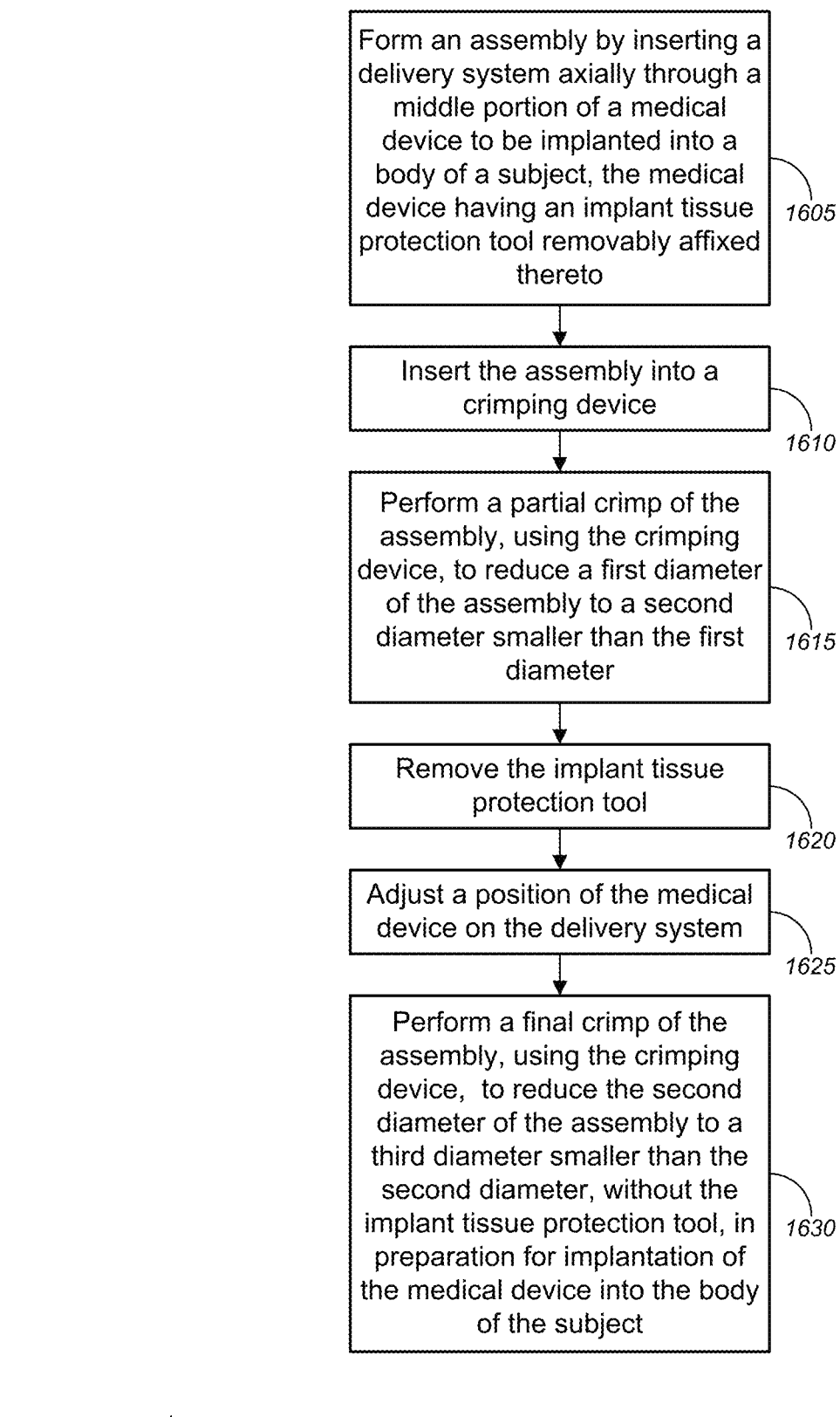
FIG. 16 is a flow diagram illustrating a method for implementing protection of at least one tissue layer of a medical device or implant during crimping of the medical device or implant prior to implantation of the medical device within a body of a subject, in accordance with various embodiments.

FIG. 16 is a flow diagram illustrating a method 1600 for implementing protection of at least one tissue layer of a medical device or implant during crimping of the medical device or implant prior to implantation of the medical device within a body of a subject, in accordance with various embodiments.

While the techniques and procedures are depicted and/or described in a certain order for purposes of illustration, it should be appreciated that certain procedures may be reordered and/or omitted within the scope of various embodiments. Moreover, while the method 1600 illustrated by FIG. 16 can be implemented by or with (and, in some cases, are described below with respect to) the systems, examples, or embodiments 100, 200, 300, 400, 500, 600, 700, 800, 900, 1000, 1100, 1200, 1300, 1400, 1400', 1400'', 1400''', 1400'''', 1400''''', and 1500 of FIGS. 1, 2, 3, 4, 5, 6, 7, 8, 9, 10, 11, 12, 13, 14A, 14B, 14C-14D, 14E-14G, 14H, and 14I, 15, respectively (or components thereof), such methods may also be implemented using any suitable hardware (or software) implementation. Similarly, while each of the systems, examples, or embodiments 100, 200, 300, 400, 500, 600, 700, 800, 900, 1000, 1100, 1200, 1300, 1400, 1400', 1400'', 1400''', 1400'''', 1400''''', and 1500 of FIGS. 1, 2, 3, 4, 5, 6, 7, 8, 9, 10, 11, 12, 13A, 13B, 13C-13D, 13E-13G, 13H-13I, and 13J, respectively (or components thereof), can operate according to the method 1600 illustrated by FIG. 16 (e.g., by executing instructions embodied on a computer readable medium), the systems, examples, or embodiments 100, 200, 300, 400, 500, 600, 700, 800, 900, 1000, 1100, 1200, 1300, 1400, 1400', 1400", 1400''', 1400'''', 1400''', and 1500 of FIGS. 1, 2, 3, 4, 5, 6, 7, 8, 9, 10, 11, 12, 13, 14A, 14B, 14C-14D, 14E-14G, 14H, and 14I, 15, can each also operate according to other modes of operation and/or perform other suitable procedures.

In the non-limiting embodiment of FIG. 16, method 1600, at block 1605, might comprise forming an assembly by inserting a delivery system axially through a middle portion of a medical device to be implanted into a body of a subject, the medical device having an implant tissue protection tool removably affixed thereto. In some embodiments, the implant tissue protection tool—which may be similar, if not identical, to the implant tissue protection tool shown and described in the one or more embodiments above with respect to FIGS. 4-12, or the like—may comprise an outer portion that is configured to surround one or more outer segments of at least one tissue layer of the medical device and at least one protrusion affixed to a first surface of the outer portion. Alternatively, the medical device having the implant tissue protection tool removably affixed thereto may be inserted into the crimping device, prior to the delivery system being inserted axially through the middle portion of the medical device.

At block 1610, method 1600 may comprise inserting the assembly into the crimping device. The implant tissue protection tool may be separate from, and may have a structure as a whole that is independent of, the crimping device. Method 1600 may further comprise performing a partial crimp of the assembly (block 1615), using the crimping device, to reduce a first diameter of the assembly to a second diameter smaller than the first diameter, wherein, during the partial crimp, the at least one protrusion actively pushes radially inward on the at least one tissue layer, thereby minimizing occurrence of the at least one tissue layer of the medical device passing through at least one opening defined at least in part by two or more struts of the medical device during crimping of the medical device; removing the implant tissue protection tool (block 1620), in some cases with the aid of separation or removal devices as shown and described above with respect to FIG. 13, or the like; and, in some cases (where necessary), adjusting a position of the medical device on the delivery system (block 1625). Method 1600 may further comprise, at block 1630, performing a final crimp of the assembly, without the implant tissue protection tool and using the crimping device, to reduce the second diameter of the assembly to a third diameter smaller than the second diameter, in preparation for implantation of the medical device into the body of the subject. Thereafter, the fully crimped assembly (without the implant tissue protection tool) may be ready for insertion into the body of the subject for delivery of the medical device.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. An implant tissue protection tool, comprising:
   an outer portion that is configured to surround one or more outer segments of at least one tissue layer of a medical device to be implanted into a body of a subject, wherein the medical device comprises a frame with a plurality of struts; and
   at least one protrusion affixed to a first surface of the outer portion, the at least one protrusion being configured to minimize occurrence of the at least one tissue layer of the medical device passing through at least one opening defined at least in part by two or more struts of the medical device during crimping of the medical device by a crimping device in preparation for implantation into the body of the subject.

2. The implant tissue protection tool of claim 1, wherein the implant tissue protection tool is separate from, and has a structure as a whole that is independent of, the crimping device.

3. The implant tissue protection tool of claim 1, wherein the outer portion comprises a sleeve that is configured to fit snugly over an outer perimeter of the medical device, wherein the at least one protrusion is configured to extend radially inward through the at least one opening that is not covered by a skirt layer of the medical device.

4. The implant tissue protection tool of claim 3, wherein the sleeve has a longitudinal length that covers at least a portion of a longitudinal length of the medical device, the longitudinal length of the sleeve being configured to at least partially cover all openings defined at least in part by struts of the medical device that are not covered by the skirt layer.

5. The implant tissue protection tool of claim 3, wherein the at least one protrusion comprises a plurality of protrusions affixed to the inner surface of the sleeve, wherein at least one protrusion among the plurality of protrusions is configured to extend through each opening defined at least in part by struts of the medical device that are not covered by the skirt layer.

6. The implant tissue protection tool of claim 5, wherein the at least one protrusion among the plurality of protrusions that is configured to extend through each opening defined at least in part by the struts of the medical device that are not covered by the skirt layer comprises two protrusions that are configured to extend through each opening.

7. The implant tissue protection tool of claim 5, wherein each of the plurality of protrusions has a length that is similar to a longitudinal length of the sleeve, wherein the length of each protrusion is aligned with the longitudinal length of the sleeve when each of the plurality of protrusions is affixed to the sleeve, and wherein the length of each of the at least one protrusion is configured to fit within each of the openings defined at least in part by struts of the medical device that are not covered by the skirt layer.

8. The implant tissue protection tool of claim 3, wherein each of the at least one protrusion has a flared hollow polygonal prism shape.

9. The implant tissue protection tool of claim 1, wherein the at least one protrusion comprises a plurality of protrusions, wherein the outer portion and the plurality of protrusions are integrally formed using a pliable material.

10. The implant tissue protection tool of claim 9, wherein the implant tissue protection tool is configured to wrap around the outer perimeter of the medical device, with the plurality of protrusions each being configured to extend through the at least one opening that is not covered by a skirt layer.

11. The implant tissue protection tool of claim 9, wherein the implant tissue protection tool is configured to be wedged between the one or more outer segments of the at least one tissue layer and the two or more struts of the medical device, with the plurality of protrusions each being configured to extend along a direction that is either parallel with or at a small angle with respect to an axis of the medical device, wherein the integrally formed outer portion and plurality of protrusions are configured to be disposed between the one or more outer segments of the at least one tissue layer and the two or more struts of the medical device, without the plurality of protrusions extending longitudinally beyond a longitudinal length of the medical device when fully wedged between the one or more outer segments of the at least one tissue layer and the two or more struts of the medical device.

12. The implant tissue protection tool of claim 1, wherein the at least one protrusion comprises a plurality of protrusions, wherein the outer portion and the plurality of protrusions are integrally formed as a flat continuous band, wherein the plurality of protrusions are each formed by folding the flat continuous band in on itself, with the outer portion being configured to wrap around an outer perimeter of the medical device and with at least one protrusion among the plurality of protrusions being configured to extend through each of the at least one opening that is not covered by a skirt layer.

13. The implant tissue protection tool of claim 1, wherein the implant tissue protection tool is made of a material that is the same as a material from which the at least one tissue layer is made.

14. The implant tissue protection tool of claim 1, wherein the implant tissue protection tool is made of a material comprising at least one of animal tissue, bovine pericardium, porcine pericardium, open-cell foam, polyurethane foam, fabric, or expanded polytetrafluoroethylene ("ePTFE").

15. The implant tissue protection tool of claim 1, wherein crimping of the medical device comprises a partial crimp that reduces a first diameter of the medical device to a second diameter smaller than the first diameter and a final crimp that reduces the second diameter of the medical device to a third diameter smaller than the second diameter, wherein the implant tissue protection tool is separated from the medical device after the partial crimp and before the final crimp.

16. The implant tissue protection tool of claim 1, further comprising:
    at least one separation device affixed to the outer portion, the at least one separation device being configured to facilitate efficient separation of the implant tissue protection tool from the medical device and to facilitate preferential orientation or folding direction of the at least one tissue layer of the medical device.

17. The implant tissue protection tool of claim 16, wherein the at least one separation device comprises a plurality of separation devices that is affixed to and arranged at intervals around an outer perimeter of the outer portion.

18. The implant tissue protection tool of claim 16, wherein the at least one separation device has a form type or shape comprising one of a side loop configuration, a bunny ear configuration, an upper tab configuration, a basket handle configuration, or a suture loop configuration.

19. The implant tissue protection tool of claim 16, wherein the at least one separation device has a general form type or shape comprising one of a loop configuration or a tab configuration.

20. A crimping system for atraumatic crimping of an implantable prosthetic valve, the crimping system comprising:
    an implantable prosthetic valve comprising a radially collapsible and expandable annular frame and a leaflet structure mounted inside the frame, the frame comprising a plurality of interconnected struts defining a plurality of open cells in the frame;
    a crimping apparatus having a plurality of crimping jaws arranged to form an aperture sized to receive the implantable prosthetic valve in a first, expanded state, to move radially inwardly to radially collapse the implantable prosthetic valve from the first, expanded state to a second, radially collapsed state during a partial crimp, and to move radially inwardly to radially collapse the implantable prosthetic valve from the second, radially collapsed state to a third, radially collapsed state during a final crimp; and
    a leaflet protection tool configured to be positioned between the plurality of crimping jaws of the crimping apparatus and the outside of the frame of the implantable prosthetic valve, the leaflet protection tool comprising:
        an outer portion that is configured to surround one or more outer segments of the implantable prosthetic valve; and
        at least one protrusion affixed to a first surface of the outer portion, the at least one protrusion being configured to minimize occurrence of the leaflet structure passing through any of the plurality of open cells in the frame during crimping of the implantable prosthetic valve by the crimping apparatus in preparation for implantation into a body of a subject, by actively pushing the leaflet structure radially inward away from the inside of the frame of the implantable prosthetic valve during the partial crimp, wherein the leaflet protection tool is separated from the implantable prosthetic valve after the partial crimp and before the final crimp.

21. The crimping system of claim 20, wherein the leaflet protection tool is made of a material that is the same as a material from which the prosthetic valve is made.

22. The crimping system of claim 20, wherein the leaflet protection tool is made of a material comprising at least one of animal tissue, bovine pericardium, porcine pericardium, open-cell foam, polyurethane foam, fabric, or expanded polytetrafluoroethylene ("ePTFE").

23. An implantable prosthetic valve system, comprising:
an implantable prosthetic valve comprising a radially collapsible and expandable annular frame and a leaflet structure mounted inside the frame, the frame comprising a plurality of interconnected struts defining a plurality of open cells in the frame; and
a leaflet protection tool configured to be positioned between a plurality of crimping jaws of a crimping apparatus and the outside of the frame of the implantable prosthetic valve, the crimping apparatus having the plurality of crimping jaws arranged to form an aperture sized to receive the implantable prosthetic valve in a first, expanded state, to move radially inwardly to radially collapse the implantable prosthetic valve from the first, expanded state to a second, radially collapsed state during a partial crimp, and to move radially inwardly to radially collapse the implantable prosthetic valve from the second, radially collapsed state to a third, radially collapsed state during a final crimp, the leaflet protection tool comprising:
an outer portion that is configured to surround one or more outer segments of the implantable prosthetic valve; and
at least one protrusion affixed to a first surface of the outer portion, the at least one protrusion being configured to minimize occurrence of the leaflet structure passing through any of the plurality of open cells in the frame during crimping of the implantable prosthetic valve by the crimping apparatus in preparation for implantation into a body of a subject, by actively pushing the leaflet structure radially inward away from the inside of the frame of the implantable prosthetic valve during the partial crimp, wherein the leaflet protection tool is separated from the implantable prosthetic valve after the partial crimp and before the final crimp.

24. The implantable prosthetic valve system of claim 23, wherein the implantable prosthetic valve further comprises an inflow portion including a plurality of inflow open cells among the plurality of open cells in the frame and an outflow portion including a plurality of outflow open cells among the plurality of open cells in the frame, wherein an area of each outflow open cell is greater than an area of each inflow open cell by a ratio of at least 1.5:1.

25. The implantable prosthetic valve system of claim 24, wherein the outflow portion further includes 6 outflow open cells per row, while the inflow portion further includes 12 inflow open cells per row.

* * * * *